(12) United States Patent
Power et al.

(10) Patent No.: US 8,283,307 B2
(45) Date of Patent: Oct. 9, 2012

(54) TREATMENT OF FIBROTIC DISEASE

(75) Inventors: Christine Power, Thoiry (FR); Yan Lavrovsky, Brookline, MA (US)

(73) Assignee: Merck Serono SA, Coinsins, Vaud (CH)

( * ) Notice: Subject to any disclaimer, the term of this patent is extended or adjusted under 35 U.S.C. 154(b) by 599 days.

(21) Appl. No.: 10/570,122

(22) PCT Filed: Sep. 7, 2004

(86) PCT No.: PCT/EP2004/052077
§ 371 (c)(1),
(2), (4) Date: Feb. 28, 2006

(87) PCT Pub. No.: WO2005/023288
PCT Pub. Date: Mar. 17, 2005

(65) Prior Publication Data
US 2007/0104723 A1    May 10, 2007

(30) Foreign Application Priority Data
Sep. 8, 2003 (EP) .................................... 03102723

(51) Int. Cl.
*A61K 38/00* (2006.01)
*A61K 38/18* (2006.01)
*A61K 38/19* (2006.01)
*C07K 14/475* (2006.01)
*C07K 14/52* (2006.01)

(52) U.S. Cl. .......... 514/1.1; 514/7.6; 530/351; 530/399; 530/387.3

(58) Field of Classification Search ................. None
See application file for complete search history.

(56) References Cited

U.S. PATENT DOCUMENTS

| 5,194,596 | A * | 3/1993 | Tischer et al. ............ 530/399 |
| 7,638,480 | B2 * | 12/2009 | Power et al. ................ 514/1.1 |
| 2007/0083334 | A1 * | 4/2007 | Mintz et al. ............... 702/19 |

FOREIGN PATENT DOCUMENTS

| WO | WO 97/46585 | 6/1997 |
| WO | WO 00/11173 | 8/1999 |
| WO | WO 01/75067 | 10/2001 |
| WO | WO 01/88088 | 11/2001 |
| WO | WO 02/074961 | 9/2002 |
| WO | WO 03/054012 | 7/2003 |

OTHER PUBLICATIONS

Yamamoto, Y. The bleomycin-induced scleroderma model: what we have learned fro scleroderma pathogenesis? Arch. Dermatol. Res. 297:333-344 (2006).*
Freshney, Culture of Animal Cells, A Manual of Basic Technique, p. 4. Alan R. Liss, Inc., New York (1983).*
Vukicevic et al. Induction of nephrogenic mesenchyme by osteogenic protein 1 (bone morphogenic protein 7). PNAS USA 93:9021-9026 (1996).*
Appel et al. Physical and transcriptional map of the critical region for keratolytic winter erythema (KWE) on chromosome 8p.22-p.23 between D8S550 and D8S1749. European Journal of Human Genetics vol. 10:17-25 (2002).*
Murrills et al. In vitro and in vivo activities of C-terminally truncated PTH peptides reveal a disconnect between cAMP singaling and functional activity. Bones 35:1263-1272 (2004).*
Twining et al. Functional characterization of arginine 30, lysine 40 and arginine 62 in Tn5 transposase. The Journal of Biological Chemistry 276/25:23135-23143 (2001).*
Grasso et al. In vivo effects of leptin-related synthetic peptides on body weight and food intake in female ob/ob mice:localization of leptin activity to domains between amino acid residues 106-140. Endocrinology, vol. 138/No. 4 (1997).*
Taimr et al. Activated stellate cells express the TRAIL receptor-2/death receptor-5 and undergo TRAIL-mediated apoptosis. Hepatology, vol. 37/No. 1, pp. 87-95 (2003).*
Yurovsky, V. V. "Tumor Necrosis Factor-Related Apoptosis-Inducing Ligand Enhances Collagen Production by Human Lung Fibroblasts" *American Journal of Respiratory Cell and Molecular Biology*, 2003, pp. 225-231, vol. 28

* cited by examiner

*Primary Examiner* — Elizabeth C Kemmerer
*Assistant Examiner* — Regina M DeBerry
(74) *Attorney, Agent, or Firm* — Saliwanchik, Lloyd & Eisenschenk

(57) ABSTRACT

The invention relates to the use of INSP035 for treatment and/or prevention of fibrotic diseases, in particular of scleroderma.

36 Claims, 3 Drawing Sheets

SEQUENCE LISTING

<160> NUMBER OF SEQ ID NOS: 20

<210> SEQ ID NO 1
<211> LENGTH: 492
<212> TYPE: DNA
<213> ORGANISM: Homo sapiens

<400> SEQUENCE: 1

```
atgtccctgg ggctactgaa attccaggca gtgggtgaag aggacgagga ggatgaggag      60
ggggagagcc tggactctgt gaaggcactg acagccaagc tgcagctgca gactcggcgg     120
ccctcatatc tggagtggac agcccaggtc cagagccagg cctggcgcag ggcccaagcc     180
aaacctggac caggggacc tggggacatc tgtggtttcg actcaatgga ctccgccctt     240
gagtggctcc gacgggagct gcgggagatg caggcgcagg acaggcagct ggcagggcag     300
```

```
ctgctgcggc tgcgggccca gctgcaccga ctgaagatgg accaagcctg tcacctgcac    360
caggagctgc tggatgaggc cgagctggag ctggagctgg agcccggggc cggcctagcc    420
ctggccccgc tgctgcggca cctgggcctc acgcgcatga acatcagcgc ccggcgcttc    480
accctctgct ga                                                        492
```

<210> SEQ ID NO 2
<211> LENGTH: 163
<212> TYPE: PRT
<213> ORGANISM: Homo sapiens

<400> SEQUENCE: 2

```
Met Ser Leu Gly Leu Leu Lys Phe Gln Ala Val Gly Glu Glu Asp Glu
1               5                   10                  15

Glu Asp Glu Glu Gly Glu Ser Leu Asp Ser Val Lys Ala Leu Thr Ala
                20                  25                  30

Lys Leu Gln Leu Gln Thr Arg Arg Pro Ser Tyr Leu Glu Trp Thr Ala
            35                  40                  45

Gln Val Gln Ser Gln Ala Trp Arg Arg Ala Gln Ala Lys Pro Gly Pro
        50                  55                  60

Gly Gly Pro Gly Asp Ile Cys Gly Phe Asp Ser Met Asp Ser Ala Leu
65                  70                  75                  80

Glu Trp Leu Arg Arg Glu Leu Arg Glu Met Gln Ala Gln Asp Arg Gln
                85                  90                  95

Leu Ala Gly Gln Leu Leu Arg Leu Arg Ala Gln Leu His Arg Leu Lys
            100                 105                 110

Met Asp Gln Ala Cys His Leu His Gln Glu Leu Leu Asp Glu Ala Glu
        115                 120                 125

Leu Glu Leu Glu Leu Glu Pro Gly Ala Gly Leu Ala Leu Ala Pro Leu
    130                 135                 140

Leu Arg His Leu Gly Leu Thr Arg Met Asn Ile Ser Ala Arg Arg Phe
145                 150                 155                 160

Thr Leu Cys
```

<210> SEQ ID NO 3
<211> LENGTH: 169
<212> TYPE: PRT
<213> ORGANISM: Homo sapiens

<400> SEQUENCE: 3

```
Met Ser Leu Gly Leu Leu Lys Phe Gln Ala Val Gly Glu Glu Asp Glu
1               5                   10                  15

Glu Asp Glu Glu Gly Glu Ser Leu Asp Ser Val Lys Ala Leu Thr Ala
                20                  25                  30

Lys Leu Gln Leu Gln Thr Arg Arg Pro Ser Tyr Leu Glu Trp Thr Ala
            35                  40                  45

Gln Val Gln Ser Gln Ala Trp Arg Arg Ala Gln Ala Lys Pro Gly Pro
        50                  55                  60

Gly Gly Pro Gly Asp Ile Cys Gly Phe Asp Ser Met Asp Ser Ala Leu
65                  70                  75                  80

Glu Trp Leu Arg Arg Glu Leu Arg Glu Met Gln Ala Gln Asp Arg Gln
                85                  90                  95

Leu Ala Gly Gln Leu Leu Arg Leu Arg Ala Gln Leu His Arg Leu Lys
            100                 105                 110

Met Asp Gln Ala Cys His Leu His Gln Glu Leu Leu Asp Glu Ala Glu
        115                 120                 125
```

```
Leu Glu Leu Glu Leu Glu Pro Gly Ala Gly Leu Ala Leu Ala Pro Leu
        130                 135                 140

Leu Arg His Leu Gly Leu Thr Arg Met Asn Ile Ser Ala Arg Arg Phe
145                 150                 155                 160

Thr Leu Cys His His His His His His
                165
```

<210> SEQ ID NO 4
<211> LENGTH: 267
<212> TYPE: DNA
<213> ORGANISM: Homo sapiens

<400> SEQUENCE: 4

```
atggactccg cccttgagtg gctccgacgg gagctgcggg agatgcaggc gcaggacagg    60
cagctggcag ggcagctgct gcggctgcgg gcccagctgc accgactgaa gatggaccaa   120
gcctgtcacc tgcaccagga gctgctggat gaggccgagc tggagctgga gctggagccc   180
ggggccggcc tagccctggc cccgctgctg cggcacctgg gcctcacgcg catgaacatc   240
agcgcccggc gcttcaccct ctgctga                                      267
```

<210> SEQ ID NO 5
<211> LENGTH: 88
<212> TYPE: PRT
<213> ORGANISM: Homo sapiens

<400> SEQUENCE: 5

```
Met Asp Ser Ala Leu Glu Trp Leu Arg Arg Glu Leu Arg Glu Met Gln
1               5                  10                  15

Ala Gln Asp Arg Gln Leu Ala Gly Gln Leu Leu Arg Leu Arg Ala Gln
            20                  25                  30

Leu His Arg Leu Lys Met Asp Gln Ala Cys His Leu His Gln Glu Leu
        35                  40                  45

Leu Asp Glu Ala Glu Leu Glu Leu Glu Leu Glu Pro Gly Ala Gly Leu
    50                  55                  60

Ala Leu Ala Pro Leu Leu Arg His Leu Gly Leu Thr Arg Met Asn Ile
65                  70                  75                  80

Ser Ala Arg Arg Phe Thr Leu Cys
                85
```

<210> SEQ ID NO 6
<211> LENGTH: 94
<212> TYPE: PRT
<213> ORGANISM: Homo sapiens

<400> SEQUENCE: 6

```
Met Asp Ser Ala Leu Glu Trp Leu Arg Arg Glu Leu Arg Glu Met Gln
1               5                  10                  15

Ala Gln Asp Arg Gln Leu Ala Gly Gln Leu Leu Arg Leu Arg Ala Gln
            20                  25                  30

Leu His Arg Leu Lys Met Asp Gln Ala Cys His Leu His Gln Glu Leu
        35                  40                  45

Leu Asp Glu Ala Glu Leu Glu Leu Glu Leu Glu Pro Gly Ala Gly Leu
    50                  55                  60

Ala Leu Ala Pro Leu Leu Arg His Leu Gly Leu Thr Arg Met Asn Ile
65                  70                  75                  80

Ser Ala Arg Arg Phe Thr Leu Cys His His His His His
                85                  90
```

```
<210> SEQ ID NO 7
<211> LENGTH: 88
<212> TYPE: PRT
<213> ORGANISM: Homo sapiens

<400> SEQUENCE: 7

Ile Asp Ser Ala Leu Glu Trp Leu Arg Arg Glu Leu Arg Glu Met Gln
1               5                   10                  15

Ala Gln Asp Arg Gln Leu Ala Gly Gln Leu Leu Arg Leu Arg Ala Gln
            20                  25                  30

Leu His Arg Leu Lys Met Asp Gln Ala Cys His Leu His Gln Glu Leu
        35                  40                  45

Leu Asp Glu Ala Glu Leu Glu Leu Glu Leu Glu Pro Gly Ala Gly Leu
    50                  55                  60

Ala Leu Ala Pro Leu Leu Arg His Leu Gly Leu Thr Arg Met Asn Ile
65                  70                  75                  80

Ser Ala Arg Arg Phe Thr Leu Cys
                85

<210> SEQ ID NO 8
<211> LENGTH: 94
<212> TYPE: PRT
<213> ORGANISM: Homo sapiens

<400> SEQUENCE: 8

Ile Asp Ser Ala Leu Glu Trp Leu Arg Arg Glu Leu Arg Glu Met Gln
1               5                   10                  15

Ala Gln Asp Arg Gln Leu Ala Gly Gln Leu Leu Arg Leu Arg Ala Gln
            20                  25                  30

Leu His Arg Leu Lys Met Asp Gln Ala Cys His Leu His Gln Glu Leu
        35                  40                  45

Leu Asp Glu Ala Glu Leu Glu Leu Glu Leu Glu Pro Gly Ala Gly Leu
    50                  55                  60

Ala Leu Ala Pro Leu Leu Arg His Leu Gly Leu Thr Arg Met Asn Ile
65                  70                  75                  80

Ser Ala Arg Arg Phe Thr Leu Cys His His His His His
                85                  90

<210> SEQ ID NO 9
<211> LENGTH: 225
<212> TYPE: DNA
<213> ORGANISM: Homo sapiens

<400> SEQUENCE: 9
atgcaggcgc aggacaggca gctggcaggg cagctgctgc ggctgcgggc ccagctgcac      60
cgactgaaga tggaccaagc ctgtcacctg caccaggagc tgctggatga ggccgagctg     120
gagctggagc tggagcccgg ggccggccta gccctggccc cgctgctgcg gcacctgggc     180
ctcacgcgca tgaacatcag cgcccggcgc ttcacccttct gctga                    225

<210> SEQ ID NO 10
<211> LENGTH: 74
<212> TYPE: PRT
<213> ORGANISM: Homo sapiens

<400> SEQUENCE: 10

Met Gln Ala Gln Asp Arg Gln Leu Ala Gly Gln Leu Leu Arg Leu Arg
1               5                   10                  15

Ala Gln Leu His Arg Leu Lys Met Asp Gln Ala Cys His Leu His Gln
```

-continued

```
                20                  25                  30

Glu Leu Leu Asp Glu Ala Glu Leu Glu Leu Glu Pro Gly Ala
            35                  40                  45

Gly Leu Ala Leu Ala Pro Leu Leu Arg His Leu Gly Leu Thr Arg Met
    50                  55                  60

Asn Ile Ser Ala Arg Arg Phe Thr Leu Cys
65                  70

<210> SEQ ID NO 11
<211> LENGTH: 80
<212> TYPE: PRT
<213> ORGANISM: Homo sapiens

<400> SEQUENCE: 11

Met Gln Ala Gln Asp Arg Gln Leu Ala Gly Gln Leu Leu Arg Leu Arg
1               5                  10                  15

Ala Gln Leu His Arg Leu Lys Met Asp Gln Ala Cys His Leu His Gln
            20                  25                  30

Glu Leu Leu Asp Glu Ala Glu Leu Glu Leu Glu Pro Gly Ala
            35                  40                  45

Gly Leu Ala Leu Ala Pro Leu Leu Arg His Leu Gly Leu Thr Arg Met
    50                  55                  60

Asn Ile Ser Ala Arg Arg Phe Thr Leu Cys His His His His His
65                  70                  75                  80

<210> SEQ ID NO 12
<211> LENGTH: 13
<212> TYPE: PRT
<213> ORGANISM: Artificial sequence
<220> FEATURE:
<223> OTHER INFORMATION: amino acid linker sequence

<400> SEQUENCE: 12

Glu Phe Gly Ala Gly Leu Val Leu Gly Gly Gln Phe Met
1               5                  10

<210> SEQ ID NO 13
<211> LENGTH: 43
<212> TYPE: DNA
<213> ORGANISM: Artificial sequence
<220> FEATURE:
<223> OTHER INFORMATION: INSP035-MF primer

<400> SEQUENCE: 13
acaaaaaagc aggcttcgaa ggagatgcca ccatgtccct ggg                43

<210> SEQ ID NO 14
<211> LENGTH: 43
<212> TYPE: DNA
<213> ORGANISM: Artificial sequence
<220> FEATURE:
<223> OTHER INFORMATION: INSP035-MR primer

<400> SEQUENCE: 14
ccccagggac atggtggcat ctccttcgaa gcctgctttt ttg                43

<210> SEQ ID NO 15
<211> LENGTH: 18
<212> TYPE: DNA
<213> ORGANISM: Artificial sequence
<220> FEATURE:
<223> OTHER INFORMATION: 21M13 primer

<400> SEQUENCE: 15
```

```
tgtaaaacga cggccagt                                                    18

<210> SEQ ID NO 16
<211> LENGTH: 18
<212> TYPE: DNA
<213> ORGANISM: Artificial sequence
<220> FEATURE:
<223> OTHER INFORMATION: M13REV primer

<400> SEQUENCE: 16
caggaaacag ctatgacc                                                    18

<210> SEQ ID NO 17
<211> LENGTH: 20
<212> TYPE: DNA
<213> ORGANISM: Artificial sequence
<220> FEATURE:
<223> OTHER INFORMATION: T7 primer

<400> SEQUENCE: 17
taatacgact cactataggg                                                  20

<210> SEQ ID NO 18
<211> LENGTH: 21
<212> TYPE: DNA
<213> ORGANISM: Artificial sequence
<220> FEATURE:
<223> OTHER INFORMATION: pDEST14-R primer

<400> SEQUENCE: 18
tggcagcagc caactcagct t                                                21

<210> SEQ ID NO 19
<211> LENGTH: 17
<212> TYPE: DNA
<213> ORGANISM: Artificial sequence
<220> FEATURE:
<223> OTHER INFORMATION: h-INSP035-169F1 primer

<400> SEQUENCE: 19
agggcccaag ccaaacc                                                     17

<210> SEQ ID NO 20
<211> LENGTH: 18
<212> TYPE: DNA
<213> ORGANISM: Artificial sequence
<220> FEATURE:
<223> OTHER INFORMATION: h-INSP035-281R1 primer

<400> SEQUENCE: 20
tcctgcgcct gcatctcc                                                    18
```

TREATMENT OF FIBROTIC DISEASE

CROSS-REFERENCE TO RELATED APPLICATION

This application is the U.S. national stage application of International Patent Application No. PCT/EP2004/052077, filed Sep. 7, 2004, the disclosure of which is hereby incorporated by reference in its entirety, including all figures, tables and amino acid or nucleic acid sequences.

FIELD OF THE INVENTION

The present invention is in the field of fibrotic diseases and connective tissue disorders. More specifically, the invention relates to the use of INSP035 for the treatment and/or prevention of fibrotic diseases, in particular scleroderma. Combinations of INSP035 with an interferon, a TNF antagonist or a further anti-fibrotic agent such as OPG and SARP-1 are also within the present invention.

BACKGROUND OF THE INVENTION

Fibrosis is a condition characterized by a deposition of extracellular matrix components in the internal organs, including the kidneys, heart, lungs, liver, skin and joints.

Lung fibrosis is one of the predominant fibrotic diseases. Idiopathic Pulmonary Fibrosis (IPF) is characterized by chronic inflammation of the alveolar walls with progressive fibrosis, of unknown etiology. IPF, or cryptogenic fibrosing alveolitis, causes 50 to 60% of cases of idiopathic interstitial lung disease (for reviews on IPF, see Khalil N and O'Connor 2004 and Selman et al. 2004).

Usual interstitial pneumonia (UIP), a specific histopathologic pattern of interstitial pneumonia, is the classic pattern found on lung biopsy in IPF. At low magnification, the tissue appears heterogeneous, with alternating areas of normal lung, interstitial inflammation, fibrosis, and honeycombing. Interstitial inflammation consists of an alveolar septal infiltrate of lymphocytes, plasma cells, and histiocytes associated with hyperplasia of type II pneumocytes. The fibrotic zones are composed mainly of dense acellular collagen, although scattered foci of proliferating fibroblasts (fibroblastic foci), which are the sites of early and active disease, may also be seen, usually in an intra-alveolar location. Areas of honeycombing are composed of cystic fibrotic airspaces, frequently lined with bronchiolar epithelium and filled with mucus. Neutrophils may pool in the mucus. Smooth muscle hyperplasia often occurs in areas of fibrosis and honeycombing. The subpleural and paraseptal distribution, patchy character, and temporal heterogeneity are the most helpful features in identifying UIP.

An identical pattern of interstitial inflammation and fibrosis occurs in collagen vascular disorders (e.g., RA, SLE, progressive systemic sclerosis, mixed connective tissue disease, diabetes mellitus), pneumoconioses (e.g., asbestosis), radiation injury, and certain drug-induced lung diseases (e.g., by nitrofurantoin).

The clinical course of IPF is progressive; median survival is 4 to 6 yr after diagnosis. Prednisone is the usual treatment in case of IPF. Response to treatment is variable, but patients with earlier disease, at a more cellular stage before scarring predominates, appear more likely to improve with corticosteroid or cytotoxic therapy. Supportive and palliative treatment includes $O_2$ in high concentrations to relieve hypoxemia and, if bacterial infection occurs, antibiotics. Lung transplantation has been successful in patients with end-stage lung disease. Fibrosis of the liver relates to an accumulation in the liver of connective tissue resulting from an imbalance between production and degradation of the extracellular matrix and accentuated by the collapse and condensation of preexisting fibers (for reviews see Afdhal NH and Nunes D. 2004. Kershenobich and Weissbrod. 2003. Pinzani and Rombouts 2004).

Liver fibrosis is a common response to hepatocellular necrosis or injury, which may be induced by a wide variety of agents, e.g., any process disturbing hepatic homeostasis (especially inflammation, toxic injury, or altered hepatic blood flow) and infections of the liver (viral, bacterial, fungal, and parasitic). Numerous storage disorders resulting from inborn errors of metabolism are often associated with fibrosis, including lipid abnormalities (Gaucher's disease); glycogen storage diseases (especially types III,. IV, VI, IX, and X); $α_1$-antitrypsin deficiency; storage of exogenous substances, as seen in iron-overload syndromes (hemochromatosis) and copper storage diseases (Wilson's disease); accumulation of toxic metabolites (as in tyrosinemia, fructosemia, and galactosemia); and peroxisomal disorders (Zellweger syndrome). Numerous chemicals and drugs cause fibrosis, especially alcohol, methotrexate, isoniazid, oxyphenisatin, methyidopa, chlorpromazine, tolbutamide, and amiodarone. Disturbances of hepatic circulation (eg, chronic heart failure, Budd-Chiari syndrome, veno-occlusive disease, portal vein thrombosis) and chronic obstruction to bile flow can lead to fibrosis. Lastly, congenital hepatic fibrosis is an autosomal recessive malformation.

The normal liver is made up of hepatocytes and sinusoids distributed within an extracellular matrix composed of collagen (predominantly types I, III, and IV) and noncollagen proteins, including glycoproteins (e.g., fibronectin, laminin) and several proteoglycans (e.g., heparan sulfate, chondroitin sulfate, dermatan sulfate, hyaluronate). Fibroblasts, normally found only in the portal tracts, can produce collagen, large glycoproteins, and proteoglycans.

Other liver cells (particularly hepatocytes and fat-storing Kupffer, and endothelial cells) also can produce extracellular matrix components. Fat-storing cells, located beneath the sinusoidal endothelium in the space of Disse, are precursors of fibroblasts, capable of proliferating and producing an excess of extracellular matrix. The development of fibrosis from active deposition of collagen is a consequence of liver cell injury, particularly necrosis, and inflammatory cells. The precise factors released from these cells is not known, but one or more cytokines or products of lipid peroxidation are likely. Kupffer cells and activated macrophages produce inflammatory cytokines. New fibroblasts form around necrotic liver cells; increased collagen synthesis leads to scarring. Fibrosis may derive from active fibrogenesis and from impaired degradation of normal or altered collagen. Fat-storing cells, Kupffer cells, and endothelial cells are important in the clearance of type I collagen, several proteoglycans, and denatured collagens. Changes in these cells' activities may modify the extent of fibrosis. For the histopathologist, fibrous tissue may become more apparent from passive collapse and condensation of preexisting fibers.

Thus, increased synthesis or reduced degradation of collagen results in active deposition of excessive connective tissue, which affects hepatic function: (1) Pericellular fibrosis impairs cellular nutrition and results in hepatocellular atrophy. (2) Within the space of Disse, fibrous tissue accumulates around the sinusoids and obstructs the free. passage of substances from the blood to the hepatocytes. (3) Fibrosis around hepatic venules and the portal tracts disturbs hepatic blood flow. Venous resistance across the liver Increases from portal vein branches to sinusoids and finally to hepatic veins. All three routes can be involved.

The fibrous bands that link portal tracts with central veins also promote anastomotic channels: Arterial blood, bypassing the normal hepatocytes, is shunted to efferent hepatic veins, which further impairs hepatic function and can accentuate hepatocellular necrosis. The extent to which these processes are present determines the magnitude of hepatic dysfunction: e.g., in congenital hepatic fibrosis, large fibrous bands involve predominantly the portal regions but usually spare the hepatic parenchyma. Congenital hepatic fibrosis thus presents as portal hypertension with preserved hepatocellular function.

Scleroderma is a disease of the connective tissue characterized by fibrosis of the skin and internal organs, leading to organ failure and death (Black et al., 1998; Clements and Furst, 1996; for reviews see Varga J. 2004. Chung and Utz, 2004. Rhew and Barr, 2004). Scleroderma has a spectrum of manifestations and a variety of therapeutic Implications. It comprises localized scleroderma, systemic sclerosis, sleroderma-like disorders, and Sine scleroderma (Smith, 2000). Whilst localized scleroderma is a rare dermatologic disease associated with fibrosis and manifestations limited to skin, systemic sclerosis is a multisystem disease with variable risk for internal organ involvement and variation in the extent of skin disease. Systemic sclerosis can be diffuse or limited. Limited systemic sclerosis is also called CREST (calcinosis, Raynaud's esophageal dysfunction, sclerodactyly, telangiectasiae). Scleroderma-like disorders are believed to be related to industrial environment exposure. In Sine disease, there is internal organ involvement without skin changes.

The major manifestations of scleroderma and in particular of systemic sclerosis are inappropriate excessive collagen synthesis and deposition, endothelial dysfunction, spasm, collapse and obliteration by fibrosis.

Scleroderma is a rare disease with a stable incidence of approximately 19 cases per 1 million persons. The cause of scleroderma is unknown. However, the genetic predisposition is important. Abnormalities involve autoimmunity and alteration of endothelial cell and fibroblast function. Indeed, systemic sclerosis is probably the most severe of the autoimmune diseases with a reported 50% mortality within 5 years of diagnosis (Silman, 1991).

In terms of diagnosis, an important clinical parameter is skin thickening proximal to the metacarpophalangeal joints. Raynaud's phenomenon is a frequent, almost universal component of scleroderma. It is diagnosed by color changes of the skin upon cold exposure. Ischemia and skin thickening are symptoms of Raynaud's disease.

Several underlying biological processes are implicated in the initiation, severity and progression of the disease and include vascular dysfunction, endothelial cell activation and damage, leukocyte accumulation, auto-antibody production and crucially, an uncontrolled fibrotic response which may lead to death (Clements and Furst, 1996). Fibroblasts have a pivotal role in the pathogenesis of this disease. Primary fibroblasts obtained from patients with scleroderma exhibit many of the characteristic properties of the disease seen in vivo, notably increased extracellular matrix synthesis and deposition, notably of collagen and fibronectin, and altered growth factor and cytokine production such as of TGFβ and CTGF (Strehlow and Korn, 1998 and LeRoy, 1974).

There is no curative treatment of scleroderma. Innovative but high-risk therapy proposed autologous stem cell transplantation (Martini et a/., 1999). In particular, there are currently no treatments for scleroderma targeting the fibrotic process (Wigley and Boling, 2000).

Identification of the genes associated with disease risk and scleroderma progression may lead to the development of effective strategies for intervention at various stages of the disease.

The secreted protein INSP035 was classified in WO03/054012 into the four-α-helix bundle cytokines subset, which is subdivided into short-chain and long-chain cytokines, as their helices comprise approximately 15 or 25 residues, respectively. Crystal structures have been determined for the long-chain four-α-helix bundle cytokines LIF, IL-6, CNTF, GH, granulocyte-colony stimulating factor (G-CSF), and leptin. Although exhibiting only a low degree of homology in their primary structures, they show a high homology in their tertiary structures and in their functional receptor epitopes. INSP035 was identified as a member of the long chain cytokine family, and more particularly, as a leptin. Sequences similar to INSP035 and its variants have been disclosed in the literature (SEQ ID NOs: 31196 and SEQ ID NO: 42492 in WO01/75067; SEQ ID NO: 13 in WO02/074961; SwissProt Acc. No. Q9BTA0). However, the experimental data provided so far do not show any involvement of these sequences in fibrotic diseases.

Osteoprotegerin (OPG) was first identified in 1997 as a novel soluble cytokine secreted by fibroblasts (Simonet et al., 1997). OPG is a member of the TNF receptor family (Morinaga et al., 1998, Yasuda et al., 1998), comprising four cysteine-rich TNFR like domains in its N-terminal portion (Simonet et al., 1997). OPG has been shown to have a role in the development of bone, and mice lacking the OPG gene had an osteoporotic phenotype and gross skeletal abnormalities (Min et al., 2000).

Osteoprotegerin, which is produced by osteoblasts and bone marrow stromal cells, lacks a transmembrane domain and acts as a secreted decoy receptor which has no direct signaling capacity. OPG acts by binding to its natural ligand osteoprotegerin ligand (OPGL), which is also known as RANKL (receptor activator of NF-kappaB ligand). The binding between OPG and OPGL binding prevents OPGL from activating its cognate receptor RANK, which is the osteoclast receptor vital for osteoclast differentiation, activation and survival. Ablation of OPGL or RANK also produces profound osteopetrosis, indicating the important physiological role of these proteins in regulating bone resorption. The secretion of OPG and OPGL from osteoblasts and stromal cells is regulated by numerous hormones and cytokines, often in a reciprocal manner. Hence, OPG might represent an effective therapeutic option for diseases associated with excessive osteoclast activity (Kostenuik and Shalhoub, 2001). In vitro, OPG was also shown to bind to another TNF family member, namely TNF-related apoptosis-inducing ligand/Apo2 ligand (TRAIL/Apo2L) with high affinity, comparable to that of binding by TRAIL-receptor(R)2 (Emery J. et al. 1998. Walczak H. et al. 1997). In addition, in a study on multiple myeloma, Shipman and Croucher showed that TRAIL/Apo2L induced apoptosis in myeloma cells, and this could be prevented with the addition of recombinant OPG (rOPG). (Shipman CM and Croucher, 2003). TRAIL induces apoptosis by cross-linking of the two TRAIL receptors that contain a death domain, TRAIL-R1 and TRAIL-R2. TRAIL-R3 and TRAIL-R4 are receptors that do not transmit an apoptotic signal.

In WO03/084560, administration of osteoprotegerin resulted in a significant amelioration of the disease in an established animal model of lung fibrosis. Lung fibrosis is one of the manifestations of scleroderma. It was therefore suggested to use osteoprotegerin for the preparation of a medicament for the treatment and/or prevention of fibrotic diseases, in particular of scleroderma. In addition, Hasel et al, in determining the expression of TRAIL and its receptors in normal pancreas and chronic pancreatitis, showed that changes in the TRAIL receptor expression were most pronounced in areas of inflammatory infiltration and active fibrosis, and that fibroblast-like cells (FLC) expressed TRAIL in areas of active fibrosis (Hasel C. et al. 2003). Taimr et al. propose that TRAIL-R2 antagonists may be useful in reducing fibrosis by inducing stellate cell apopotosis on the ground that TRAIL-R2 is not expressed by hepatocytes (Taimr P. et al. 2003). This is based on the observation that apoptosis represents an important mechanism to reduce numbers of activated stellate cells during the resolution phase of hepatic fibrosis. Furthermore, Yurovsky showed that both alpha2(I) collagen mRNA level and total soluble collagen secretion by normal human lung fibroblasts were increased upon TRAIL stimulation at low concentrations, whereas high concentrations of TRAIL was found to induce apoptotic death of these cells. He suggested also that TRAIL enhances extracellular matrix synthesis by triggering TGFβ production that acts in an autocrine manner (Yurovsky V V., 2003.).

SUMMARY OF THE INVENTION

The invention is based on the finding that INSP035 is a potent inhibitor of TRAIL in an in vitro assay designed to select anti-apoptotic molecules in fibroblasts with osteoprotegerin (OPG) as control. Hence, like OPG, INSP035 is able to counteract the apoptotic effect of soluble human recombinant TRAIL on fibroblasts, thereby consistently reducing fibroblasts' apoptosis.

It is therefore a first object of the invention to use INSP035 for the preparation of a medicament for the treatment and/or prevention of fibrotic diseases, in particular of scleroderma. It is a second object of the invention to use a cell expressing INSP035, or an expression vector comprising the coding sequence of INSP035, for the preparation of a medicament for the treatment and/or prevention of a fibrotic disease, in particular systemic sclerosis. Pharmaceutical compositions comprising INSP035 and further anti-fibrotic drugs, such as halofuginone, OPG, or SARP-1, and methods of treatment comprising administering INSP035 to the human body are also within the scope of the present invention.

DESCRIPTION OF THE INVENTION

Figure 1:
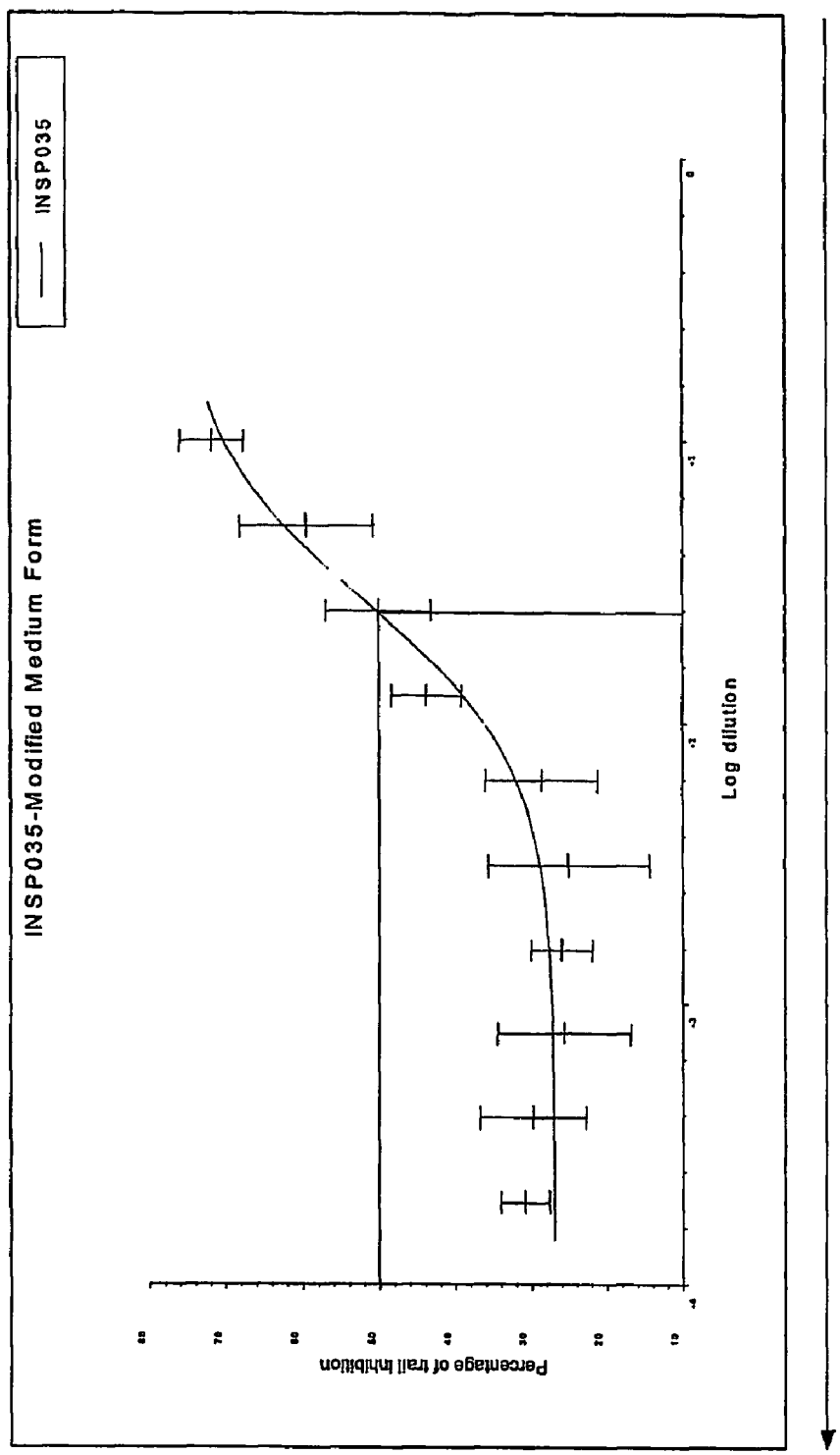
FIG. 1. INSP035-His Modified Medium Long Form (SEQ ID NO: 8) in TRAIL assay. Y-axis represents the percentage of TRAIL inhibition. X-axis represents the log dilution of the modified medium form of INSP035. Similar curves were obtained with SEQ ID NO: 3 (INSP035-His Long Form) and SEQ ID NO: 6 (INSP035-His Medium Form).

The invention is based on the finding that INSP035 is a potent inhibitor of TRAIL in an in vitro assay designed to select anti-apoptotic molecules in fibroblasts with osteoprotegerin (OPG) as control. Hence, like OPG, INSP035 Is able to counteract the apoptotic effect of soluble human recombinant TRAIL on fibroblasts, thereby consistently reducing fibroblasts' apoptosis (see FIG. 1). In the same assay, the leptin protein did not affect TRAIL-mediated apoptosis, showing no effect at all (see FIG. 2).

WO03/084560 showed that administration of osteoprotegerin resulted in a significant amelioration of fibrosis in an established animal model of lung fibrosis (see also Hasel et al. and Taim et al. in section "Background of the invention"). On the basis that OPG and INSP035 share common functionalities and on the findings that TRAIL stimulate collagen production (Yurovsky V V. 2003), INSP035 is suggested to be useful in the treatment of fibrosis. Although we do not want to be bound by theories, an hypothesis on the mechanism of action of INSP035 is proposed on the basis of our results in which INSP035, as a TRAIL inhibitor, might lower the amount of TGFβ present in the cells, which in turn would reduce collagen synthesis known to be deleterious in the pathogenesis of fibrosis.

Therefore, the invention relates to the use of a polypeptide for the manufacture of a medicament for the treatment and/or prevention of a fibrotic disease, wherein said polypeptide is selected from the group consisting of:
a) A polypeptide as set forth in any of SEQ ID NO: 2, SEQ ID NO: 5, SEQ ID NO: 7, or SEQ ID NO: 10;
b) The histidine tag form of the polypeptides whose sequences are recited in SEQ ID NO: 2 (SEQ ID NO: 3) or SEQ ID NO: 5 (SEQ ID NO: 6) or SEQ ID NO: 7 (SEQ ID NO: 8) or SEQ ID NO: 10 (SEQ ID NO: 11);
c) A polypeptide comprising any of SEQ ID NO: 2, SEQ ID NO: 3, SEQ ID NO: 5, SEQ ID NO: 6, SEQ ID NO: 7, SEQ ID NO: 8, SEQ ID NO: 10 or SEQ ID NO: 11;
d) A mutein of any of (a) to (c), wherein the amino acid sequence has at least 40% or 50% or 60% or 70% or 80% or 90% id entity to at least one of the sequences in (a) to (c);
e) A mutein of any of (a) to (c) wherein any changes in the amino acid sequence are conservative amino acid substitutions to the amino acid sequences in (a) to (c);
f) A salt or an isoform, fusion protein, functional derivative, active fraction or circularly permutated derivative of any of (a) to (e).

The invention further relates to the use of a nucleic acid molecule for the manufacture of a medicament for the treatment and/or prevention of a fibrotic disease, wherein said nucleic acid molecule comprises a nucleic acid sequence encoding a polypeptide as set forth in any of SEQ ID NO: 2, SEQ ID NO: 3, SEQ ID NO: 5, SEQ ID NO: 6, SEQ ID NO: 7, SEQ ID NO: 8, SEQ ID NO: 10 or SEQ ID NO: 11 and comprising a nucleic acid sequence selected from the group consisting of:
a) A nucleic acid sequence as set forth in any of SEQ ID NO: 1, SEQ ID NO: 4, or SEQ ID NO: 9;
b) A nucleic acid sequence which hybridizes to the complement of the nucleic acid sequence of (a) under moderately stringent conditions or under highly stringent conditions;
c) A nucleic acid sequence of any of (a) or (b) wherein said nucleic acid sequence encodes an amino acid sequence having conservative amino acid substitutions to the amino acid sequences in SEQ ID NO: 2, SEQ ID NO: 3, SEQ ID NO: 5, SEQ ID NO: 6, SEQ ID NO: 7, SEQ ID NO: 8, SEQ ID NO: 10 or SEQ ID NO: 11.

It will be appreciated by the person skilled in the art that in accordance with the present invention, a substance which stimulates release or potentiates the activity of endogenous INSP035 can equally be used for treatment and/or prevention of fibrotic disease, in particular of scleroderma. Said substance may be INSP035 itself, or any fragment of INSP035 able to inhibit TRAIL.

The full length cDNA of human INSP035 (INSP035 Long Form) has been cloned and is depicted as SEQ ID NO: 1 of the attached sequence listing. The corresponding amino acid sequence is given as SEQ ID NO: 2 of the attached sequence listing. The cDNA of human INSP035 starting at the second methionine (INSP035 Medium Form) from INSP035 Long Form has been cloned and is depicted as SEQ ID NO: 4 of the attached sequence listing. The corresponding amino acid sequence is given as SEQ ID NO: 5 of the attached sequence listing. A modified INSP035 Medium Form with an isoleucine substitution at position 1 (Met->Ile) has been generated with the amino acid sequence given in SEQ ID NO: 7. The cDNA of human INSP035 starting at the third methionine (INSP035 Short Form) from INSP035 Long Form has been cloned and is depicted as SEQ ID NO: 9 of the attached sequence listing. The corresponding amino acid sequence is given as SEQ ID NO: 10 of the attached sequence listing.

The term "treatment and/or prevention" as used herein encompasses any attenuation, reduction, or partial, substantial or complete prevention or blockage of disease formation, development, progression or of the formation, development or progression of any one or several or all of the symptoms of the disease.

The term "fibrotic disease" as used herein relates to diseases involving fibrosis, which may e.g. be due to chronic inflammation or repair and reorganization of tissues. Fibrosis may involve any organ of the human body, such as e.g. the skin, lung, pancreas, liver or kidney. Therefore, the invention also relates to treatment and/or prevention of fibrotic diseases such as liver fibrosis, liver cirrhosis, lung fibrosis, interstitial pulmonary fibrosis, Dupuytren's contracture, keloid and other scarring/wound healing abnormalities, postoperative adhesions and reactive fibrosis, as well as chronic heart failure, in particular after myocardial infarction. Further diseases or disorders treatable with INSP035 comprise wound-healing diseases, in particular wound healing in the lung, comprising chronic inflammation of the lung and ultimately fibrosis or scarring of lung surfaces. Disorders involving inflammation of the lung comprise e.g. idiopathic pulmonary fibrosis, sarcoidosis, bronchopulmonary dysplasia, fibroproliferative ARDS, as well as pulmonary manifestations or systemic diseases such as rheumatoid arthritis (Krein et al., 2001).

Fibrosis generally involves generation or proliferation of connective tissue, which replaces functional specialized tissue of a given organ. Therefore, in a preferred embodiment of the present invention, the fibrotic disease is a connective tissue disease.

In a preferred embodiment, the connective tissue disease is scleroderma.

The term "scleroderma" as used herein relates to a disease also called systemic sclerosis or systemic scleroderma. These terms are used synonymously within the present patent application. Systemic sclerosis is a chronic disease of unknown cause, characterized by diffuse fibrosis; degenerative changes; and vascular abnormalities in the skin, articular structures, and internal organs (especially the esophagus, gastrointestinal tract, lung, heart, and kidney, for example). It may be localized, or mixed, systemic, limited or diffuse.

The term "scleroderma" preferably relates to localized, systemic, limited and diffuse scleroderma as well as overlap syndromes.

Localized scleroderma primarily affects the skin, but may also affect the underlying muscles and bones. However, it generally does not affect internal organs. Localized scleroderma is relatively mild, and may be related to systemic scleroderma in terms of similar superficial symptoms, such as the appearance of skin biopsy under the microscope.

Systemic scleroderma comprises several types of symptoms or groups of symptoms, such as CREST, limited and diffuse. It may also be referred to as progressive systemic sclerosis, or familial progressive systemic sclerosis. Systemic scleroderma may e.g. affect the skin, blood vessels, and/or internal organs. When it affects the skin, it can cause the skin to harden, most commonly on the hands and/or face. When it affects the blood vessels, it can cause Raynaud's disease. The most serious forms of systemic sclerosis affect the internal organs, and may cause disability or even death. Among others, systemic sclerosis comprises: scleroderma lung disease, scleroderma renal crisis, cardiac manifestations, muscular weakness including fatigue or limited CREST, gastrointestinal dysmotility and spasm, and abnormalities in the central, peripheral and autonomic nervous system. With regard to the nervous system abnormalities, carpal tunnel syndrome followed by trigeminal neuralgia are the most common.

Limited Scleroderma may e.g. be limited to the hands, although the face and neck may also be involved.

Diffuse Scleroderma comprises skin tightening and also occurs above the wrists (or elbows). There are several subcategories of diffuse systemic sclerosis, such as "scleroderma sine scleroderma" where there is internal organ fibrosis, but no skin tightening; and familial progressive systemic sclerosis, a rare form occurring in families.

Overlap syndromes are referred to if a scleroderma patient also has other autoimmune disease (such as lupus, rheumatoid arthritis, etc.), as e.g. in diffuse scleroderma in overlap with lupus. Scleroderma symptoms can also be a part of mixed connective tissue disease (MCTD), or Undifferentiated Connective Tissue Disease (UCTD).

The term "INSP035" as used herein, relates to a protein comprising all, or a portion of the sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11 (all human) of the enclosed sequence listing, as well as to salts, isoforms, muteins, active fractions, functional derivatives and circularly permutated derivatives thereof. INSP035 from species other than human, such as mouse or rat, may be used in accordance with the present invention, as long as there is a sufficient identity between the proteins as to allow the protein to exhibit its biological activity, and without eliciting a substantial immune response in a human being.

The term "INSP035", as used herein, further relates to any fragment, portion, domain or sub-domain of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11 showing the desired activity in scleroderma or other fibrotic diseases. Protein fragments, isoforms, differentially glycosylated or sialylated forms or one or more domains of the protein may be used according to the invention, as long as they exhibit any beneficial effect on fibrotic disease, preferably an effect which is at least comparable of the full length protein. The beneficial effect can be measured in one of the in vitro or in vivo tests described in the examples below, or in any other assay adequate to demonstrate an effect in fibrotic diseases, in particular of scleroderma.

In accordance with the present invention, INSP035 can be a naturally occurring, i.e. native protein, or a recombinant protein. Recombinant production may be carried out in eukaryotic cells, such as yeast cells or mammalian cells, preferably in CHO cells, HEK cells (human embryonic kidney cells) or in human fibroblast cells or cell lines. It may further be produced in prokaryotic cells such as *E. coli.*

Preferably, INSP035 is glycosylated at one or more sites. It may also be unglycosylated, depending on the given needs and the source of production or isolation of the protein.

The term "salts" herein refers to both salts of carboxyl groups and to acid addition 20 salts of amino groups of INSP035 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of INSP035 relevant to the present invention, i.e., exert a beneficial effect on fibrotic diseases, in particular scleroderma.

Isoforms or splice variants of INSP035 may also be used according to the 30 invention, as long as they are capable of inhibiting disease progression and/or symptoms of that disease.

As used herein the term "muteins" refers to analogs of INSP035, in which one or more of the amino acid residues of natural INSP035 are replaced by different amino acid residues, or are deleted, or one or more amino acid residues are added to the natural sequence of INSP035, having preferably at least the same activity as wild type INSP035 or even having a much more potent activity. The biological activity of INSP035 can e.g. be measured by assaying INSP035 in its capacity to inhibit TRAIL. Assays for assessing protein-protein interactions are well known by the person skilled in the art. Examples for such assays are ELISA type binding assays, immuno-precipitation assays, or measurement in any other suitable system such as the BIAcore system. These muteins are prepared by known synthesis and/or by site-directed mutagenesis techniques, or any other known technique suitable therefor.

Any such mutein preferably has a sequence of amino acids sufficiently duplicative of that INSP035, such as to have at least a substantially similar activity of INSP035. The activity of an INSP035 mutant can further be tested in the assays explained in the example below (example 2) or in the examples described in WO03/084560. Measuring the amount of collagen synthesis in fibroblasts treated with INSP035 may be a suitable test for assessing the activity of INSP035 muteins, for example.

Muteins in accordance with the present invention include proteins encoded by a nucleic acid, such as DNA or RNA, which hybridizes to DNA or RNA, which encodes INSP035, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2 ×SSC and 0.5% SDS for 5 minutes, 2 ×SSC and 0.1% SDS for 15 minutes; 0.1 ×SSC and 0.5% SDS at 37° C. for 30-60 minutes and then, a 0.1 ×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of INSP035, such as to have substantially similar, or even better, biological activity as INSP035.

One easily measurable activity of INSP035 is its capability of reducing collagen synthesis. As long as the mutein has substantial collagen reducing activity, it can be considered to have substantially similar activity to INSP035. Thus, it can be determined whether any given mutein has at least substantially the same activity as INSP035 by means of routine experimentation comprising subjecting such a mutein.

In a preferred embodiment, any such mutein has at least 40% identity or homology with the sequence of INSP035. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al, 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at See Worldwide Website.ncbi.nim.nlh.gov) and FASTA (Pearson W R, 1990; Pearson 1988).

Muteins of INSP035, which can be used in accordance with the present invention, or nucleic acids encoding them, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of INSP035 polypeptides or proteins, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |

TABLE III-continued

Most Preferred Groups of Synonymous Amino Acids

| Amino Acid | Synonymous Group |
|---|---|
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of INSP035 polypeptides or proteins, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

The term "fusion protein" refers to a polypeptide comprising INSP035, or a mutein thereof, fused with another protein, which, e.g., has an extended residence time in body fluids. Fusion proteins comprising all or a functional part of INSP035 fused to all or a functional part of a protein capable of improving the biological activities of the molecule, like half-life in the human body, for instance, are preferred according to the invention. In a preferred embodiment the fusion protein comprises an immunoglobulin (Ig) fusion. Fusion proteins comprising all or part of INSP035 fused to all or part of an immunoglobulin are highly preferred. They can be monomeric or multimeric, hetero- or homomultimeric. Advantageously, the fusion protein comprises the constant region of an immunoglobulin, in particular of the Fc portion of the immunoglobulin. Embodiments in which the immunoglobulin is of the IgG1 or IgG2 isotype are further preferred according to the invention. Preferably, the fusion is an Fc fusion.

INSP035 may thus be fused to another protein, polypeptide or the like, e.g., an immunoglobulin or a fragment thereof. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:12) introduced between the INSP035 sequence and the immunoglobulin sequence.

"Functional derivatives" as used herein cover derivatives of INSP035, and their muteins and fusion proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is at least substantially similar to the activity of INSP035, and do not confer toxic properties on compositions containing it. Therefore, In a preferred embodiment the functional derivative comprises at least one moiety attached to one or more functional groups, which occur as one or more side chains on the amino acid residues.

In accordance with the present invention, polyethylene glycol (PEG) side-chains are highly preferred moieties. PEG side chains may mask antigenic sites and extend the residence of the substance they are attached to in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

"Active fractions" of INSP035 and its muteins and fusion proteins, cover any fragment or precursors of the polypeptide chain of the protein molecule alone or together with associated molecules or residues linked thereto, e.g., sugar or phosphate residues, or aggregates of the protein molecule or the sugar residues by themselves, provided said active fraction has at least a substantially similar activity to INSP035.

In accordance with the present invention, INSP035 may also be administered to the human body in form of a vector comprising said nucleic acid molecule. Therefore, the invention further relates to the use of a vector comprising said nucleic acid molecule for the manufacture of a medicament for the treatment and/or prevention of scleroderma or another fibrotic disorder Preferably, the vector is an expression vector, comprising a promoter operably linked to all or part of the coding sequence of INSP035. In a further preferred embodiment, the vector is a gene therapy vector. Gene therapy vectors are known in the art, most of them are virally derived vectors, such as adenoviral or lentiviral vectors.

According to the invention, INSP035 may also be administered to the human body in form of a cell producing and/or secreting INSP035. Therefore, the invention further relates to the use of a cell expressing INSP035 for the manufacture of a medicament for the treatment and/or prevention of scleroderma or any other fibrotic disease, i.e. to cell therapy for the treatment and/or prevention of scleroderma or other fibrotic diseases. The cell may be a naturally producing INSP035 and/or a transfected cell that produces recombinant INSP035. Preferred are cells expressing and secreting high amounts of the protein, such as over-expressing cells carrying high copy numbers of an expression vector comprising a nucleic acid molecule encoding INSP035.

As fibroblasts represent the machinery of fibrosis they are the most suitable cells for anti-fibrotic and scleroderma therapy. Therefore, preferably, INSP035 expressing fibroblasts are used in accordance with the present invention.

The invention further relates to a cell comprising a vector comprising a nucleic acid molecule encoding all or part of INSP035 for the preparation of a medicament for treatment and/or prevention of fibrotic disease, in particular of scleroderma. A cell that has been genetically modified to produce a polypeptide according to the invention is also within the scope of the present invention.

The use of an expression vector for inducing and/or enhancing the endogenous production of INSP035 in a cell normally silent or expressing amounts of the inhibitor which are not sufficient, are also contemplated according to the invention. Thus, the invention makes use of a technology known as endogenous gene activation (EGA) for the production of the desired protein.

Figure 3:
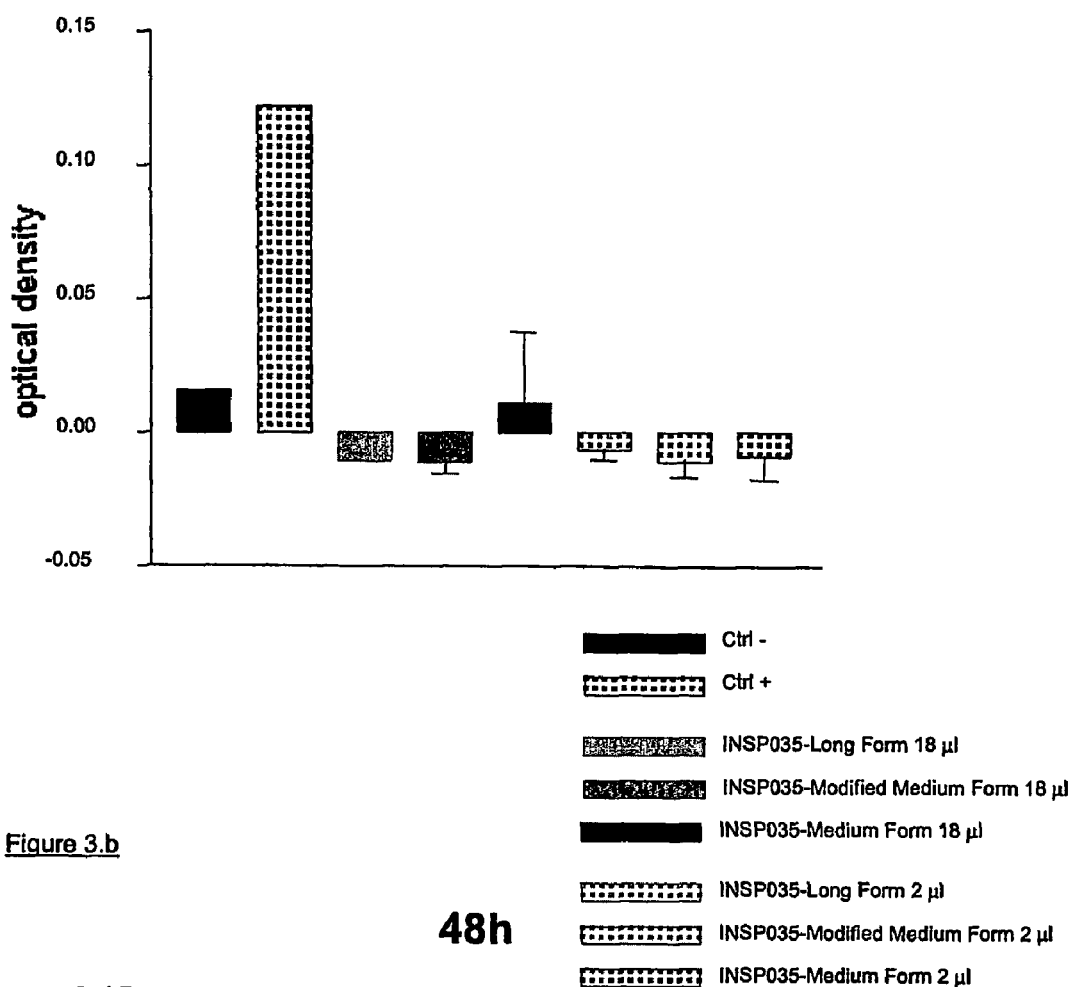
FIG. 3. Effect of INSP035 on mouse OPG 24 hours (A) or 48 hours (B) after INSP035's addition. In each figures, Y-axis represents the optical density and the X-axis the different assays performed starting with negative and positive controls followed by the various forms of INSP035 tested subdivided in two categories depending on the amount of INSP035 added (18 μl or 2 μl respectively).

It was also shown here that INSP035 doesn't induce endogenous OPG expression, indicating that INSP035 is not acting through OPG (FIG. 3). This suggests that the use of the combination of INSP035 and OPG might act in an additive or synergistic manner In the treatment of fibrosis. In the same way, several other treatments can be combined with INSP035 to obtain an additive or synergistic effect in accordance with the present invention Therefore, preferably, the medicament of the invention further comprises:

Osteoprotegerin (OPG)

Interferon, in particular interferon-β

A Tumor Necrosis Factor (TNF) antagonist, in particular soluble TNFRs, such as soluble p55 (TBPI) and/or soluble p75 (TBP II);

A further anti-scleroderma agent;

An anti-scleroderma agent selected from the group consisting of halofuginone, ACE inhibitors, calcium channel blockers, proton pump inhibitors, NSAIDs such as ibuprofen, COX-inhibitors, corticosteroids such as prednisone, tetracycline, pentoxifylline, bucillamine, geranylgeranyl transferase inhibitors, rotterlin, prolyl-4-hydroxlase inhibitors, c-proteinase inhibitors, lysyl-oxidase inhibitors, relaxin, halofuginone, prostaglandins, prostacydins, endothelin-1, nitric oxide, angiotensin II inhibitors, interleukin-10, interleukin-8, leukotriene B4, ursodeoxycholic acid, anti-oxidants or SARP-1.

SARP-1 is a protein shown to have a beneficial effect in fibrotic diseases such as scleroderma (WO02/46225). Fragments, isoforms, active fractions, fusion proteins or functional derivatives of SARP-1, as described in WO02/46225, may also be used in combination with INSP035, in accordance with the present invention.

All treatments are intended for simultaneous, sequential or separate use.

Pharmaceutical compositions comprising one or more of the above substances, together with INSP035, are within the scope of the present invention.

Although there is presently no cure for scleroderma, several agents or treatments are presently being used to treat scleroderma symptoms. Such anti-scleroderma agents, which may be used as combination therapy according to the invention, are summarized e.g. in Leighton (2001) or Wigley and Sule (2001), which are fully incorporated by reference herein.

Interferons are predominantly known for inhibitory effects on viral replication and cellular proliferation. Interferon-γ, for example, plays an important role in promoting immune and inflammatory responses. Interferon β (IFN-β, an interferon type I), is said to play an anti-inflammatory role.

In yet a further embodiment of the invention, INSP035 is used in combination with a TNF antagonist. TNF antagonists exert their activity in several ways. First, antagonists can bind to or sequester the TNF molecule itself with sufficient affinity and specificity to partially or substantially neutralise the TNF epitope or epitopes responsible for TNF receptor binding (hereinafter termed "sequestering antagonists"). A sequestering antagonist may be, for example, an antibody directed against TNF.

Alternatively, TNF antagonists can inhibit the TNF signalling pathway activated by the cell surface receptor after TNF binding (hereinafter termed "signalling antagonists"). TNF antagonists are easily identified and evaluated by routine screening of candidates for their effect on the activity of native TNF on susceptible cell lines in vitro, for example human B cells, in which TNF causes proliferation and immunoglobulin secretion. The assay contains TNF formulation at varying dilutions of candidate antagonist, e.g. from 0,1 to 100 times the molar amount of TNF used in the assay, and controls with no TNF or only antagonist (Tucci et al., 1992).

Sequestering antagonists are the preferred TNF antagonists to be used according to the present invention. Amongst sequestering antagonists, those polypeptides that bind TNF with high affinity and possess low immunogenicity are preferred. Soluble TNF receptor molecules and neutralising antibodies to TNF are particularly preferred. For example, soluble forms of TNF-RI (p55) and TNF-RII (p75) are useful in the present invention. Truncated forms of these receptors, comprising the extracellular domains of the receptors or functional portions thereof, are more particularly preferred antagonists according to the present invention. Truncated soluble TNF type-I and type-II receptors are described in EP914431, for example.

Truncated forms of the TNF receptors are soluble and have been detected in urine and serum as about 30 kDa or 40 kDa TNF inhibitory binding proteins, which are called TBPI and TBPII, respectively (Engelmann et al., 1990). The simultaneous, sequential, or separate use of INSP035 with the TNF antagonist and/or an Interferon is preferred, according to the invention.

According to the invention, TBPI and TBPII are preferred TNF antagonists to be used in combination with an INSP035. Derivatives, fragments, regions and biologically active portions of the receptor molecules functionally resemble the receptor molecules that can also be used in the present invention. Such biologically active equivalent or derivative of the receptor molecule refers to the portion of the polypeptide, or of the sequence encoding the receptor molecule, that is of sufficient size and able to bind TNF with such an affinity that the interaction with the membrane-bound TNF receptor is inhibited or blocked.

In a further preferred embodiment, human soluble TNF-RI (TBPI) is the TNF antagonist to be used according to the invention. The natural and recombinant soluble TNF receptor molecules and methods of their production have been described in the European Patents EP 308 378, EP 398 327 and EP 433 900.

Whilst it may be beneficial to block TNF-α in early stages of the disease, it has been discussed that in later stages, TNF itself may exert a beneficial effect on scleroderma (Abraham et al., 2000). Therefore, the invention further relates to a combination of INSP035 and TNF for treatment or prevention of scleroderma, in particular in advanced stages of disease. TNF-α or TNF-β may be used in accordance with the invention.

The Invention further relates to a pharmaceutical composition comprising INSP035, optionally together with one or more pharmaceutically acceptable carriers, diluents or excipients, for the treatment and/or prevention of fibrotic disease, in particular scleroderma. The pharmaceutical composition may further comprise any of the above-identified further components, and in particular an interferon, a TBP or a COX inhibitor.

The pharmaceutical composition according to the invention may also comprise a vector comprising a nudeic acid molecule according to the invention, or a cell expressing INSP035.

The active ingredients of the pharmaceutical, i.e. polypeptides, nucleic acids or cells according to the invention, or combinations thereof, as well as the combinations of substances mentioned above, may be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amount of the active protein(s) will be a function of many variables, including the type of receptor, the affinity of the substance according to the invention to its receptor, any residual cytotoxic activity exhibited thereby, the route of administration, the clinical condition of the patient.

A "therapeutically effective amount" is such that when administered, the substance according to the invention results in a beneficial effect on disease development or progression in vivo. The dosage administered, as single or multiple doses, to an individual will vary depending upon a variety of factors, including the pharmacokinetic properties of INSP035, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art.

The dose of the polypeptide according to the invention required will vary from about 0,0001 to 100 mg/kg or about 0.01 to 10 mg/kg or about 0.1 to 5 mg/kg or about 1 3 mg/kg, although as noted above this will be subject to a great deal of therapeutic discretion. The medicament of the invention may be administered daily, every other day, or three times per week.

The daily doses are usually given in divided doses or in sustained release form effective to obtain the desired results. Second or subsequent administrations can be performed at a dosage, which is the same, less than or greater than the initial or previous dose administered to the individual. A second or subsequent administration can be administered during or prior to onset of the disease.

The invention further relates to a method for treating and/or preventing fibrotic diseases, in particular scleroderma, comprising administering to a patient in need thereof an effective amount of a substance according to the invention, optionally together with a pharmaceutically acceptable carrier. Alternatively, or additionally, a cell producing INSP035 or a nucleic acid molecule of the invention, optionally comprised in an expression vector, may be administered according to the invention.

The expression vector may be administered systemically. Preferably the expression vector is administered by intramuscular injection. A further preferred route of administration is inhalation, in particular if lung fibrosis is involved in the disease. Topical administration of an expression vector comprising INSP035 sequences, or of an INSP035 polypeptide according to the invention, is a further preferred route of administration, in particular if there is an involvement of the skin.

The invention further relates to a method for the preparation of a pharmaceutical composition comprising admixing an effective amount of INSP035 with a pharmaceutically acceptable carrier, and to a method of treatment and/or prevention of arthritis comprising administering to a host in need thereof an effective inhibiting amount of INSP035.

All references cited herein, including journal articles or abstracts, published or unpublished patent applications, issued patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are Intended to be within the meaning an range of equivalents of the disposed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Having now described the invention, it will be more readily understood by reference to the following examples that are provided by way of illustration and are not intended to be limiting of the present invention.

EXAMPLES

Example 1

Cloning and Expression

Cloning of INSP035, construction of plasmids for expression of INSP035 in HEK293/EBNA cells, Identification of cDNA libraries/templates containing INSP035 and the expression of INSP035-Long-6HIS-V1 in mammalian cells are described in Example 1 and Example 2 of WO03/054012.

Example 2

INSP035's Neutralization of Apoptosis in Fibroblasts Treated with Soluble Human Recombinant TRAIL 2.1 Introduction TNF-related apoptosis-inducing ligand (TRAIL) has been shown to be one of the cellular ligands for osteoprotegerin (OPG). A secondary assay mimicking this physiological interaction in fibroblasts was developed. This assay, neutralization of apoptosis in fibroblasts treated with soluble human recombinant TRAIL, is indicated to select potentially novel TRAIL receptors and novel proteins and small molecules with anti-apoptotic activity.

2.2 Equipments and Softwares

96 Well tissue culture plate (ref costar no 3596)
96 plate reader with 490 nm filter
Graph Pad Prism software 2.3 Materials and Reagents L929 mouse fibroblast cells (CCL-1)
(American Type culture collection ATCC)
DMEM (32430-027) Gibco BRL
Sterile fetal bovine serum
Actinomycin D (FLUKA ref 01817)
Recombinant Human Trail/TNFS10
Cytotox 96 Non radioactive (Promega G179A)
Osteoprotegerin (positive control)
INSP035

2.4 Cell Culture

The cells were grown until they reached confluence. The cells were then trypsinized and seeded in DMEM 2% FCS at 20,000 cells/well. The final volume was 100 µl/well. The solution was then incubated overnight at 37° C. in a 5% CO2 humidified chamber. The medium was changed with DMEM 2% FCS with actinomycin D at a final concentration of 1 µg/ml. 2 ng/ml of rTRAIL (375TEC) was thereafter added to induce apoptosis and incubated 24 h in a 5% CO2 humidified chamber. The conditioned media was then removed and the samples were taken for the cytotoxicity assay.

For the cytotoxicity assay, apoptosis was always measured in the presence of rTRAIL. The positive effector was therefore 2 ng/ml TRAIL. The reference molecule OPG (10 ng/ml), INSP035 or leptin were added 30 minutes before the addition of TRAIL.

2.5 Cytotoxicity Assay

The cytotoxicity assay is a calorimetric assay measuring production of lactate dehydrogenase.

Firstly, 50 µl of the supernatant was transferred in the plate. Secondly, the assay buffer was used to reconstitute the substrate mix. Then, 50 µl of reconstituted substrate mix was added to each well of the supernatant. The plate was thereafter covered and incubated for 30 minutes at room temperature, protected from light. 50 µl of stop solution was then added to each well and the absorbance recorded at 490 nm.

2.6 OPG Enzyme Immunoassay

To check whether INSP035 stimulates endogenous OPG production or not, L929 cells were cultured in 96-well plates with various amounts of INSP035 variants (as described for the cytotoxicity assay). 50 µl of the conditioned media were taken for the OPG production assay. The OPG ELISA kit (BIOMEDICA, Cat. No. BI-20402) was used to measure OPG production at 24 hours and 48 hours after INSP035 treatment.

2.7 Conclusion

Figure 2:
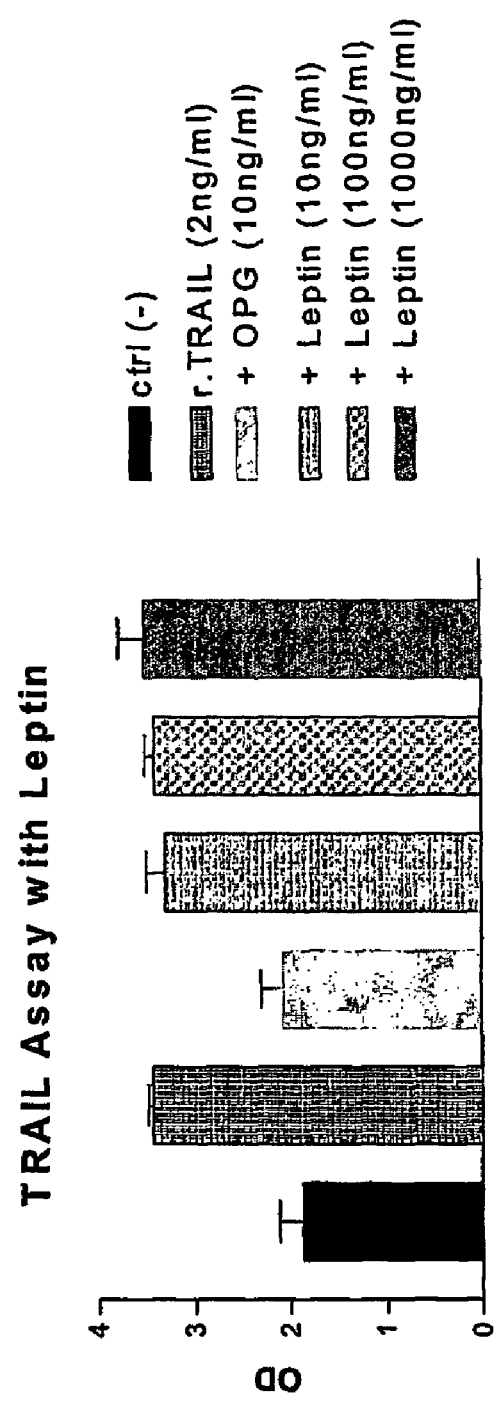
FIG. 2. LEPTIN in TRAIL assay. Y-axis represents the optical density. X-axis represents the different assays performed, starting with the negative control, then recombinant TRAIL, followed by osteoprotegerin, and finally leptin at various concentrations (10 ng/ml, 100 ng/ml and 1000 ng/ml).

INSP035 and its variants are potent inhibitors of TRAIL in an in vitro assay designed to select anti-apoptotic molecules in fibroblasts with osteoprotegerin (OPG) as control (see FIG. 1; similar curves were obtained with the other variants). Hence, like OPG, INSP035 is able to counteract the apoptotic effect of soluble human recombinant TRAIL on fibroblasts, thereby consistently reducing fibroblasts' apoptosis. In the same assay, leptin did not affect TRAIL-mediated apoptosis (FIG. 2).

Results of the OPG enzyme immunoassay suggest that INSP035, acting through a different pathway than OPG, is likely to act in an additive or synergistic manner with OPG in the treatment and/or prevention of fibrotic disease.

Based on the above findings and on the fact that TRAIL stimulates collagen production, it is suggested that INSP035 might prove useful in the treatment and/or prevention of fibrotic disease.

Example 3

Generation of an E. coli Expression Construct for INSP035

A Gateway™ cloning system compatible plasmid, pENTR-INSP035-6HIS was mutated by site-directed mutagenesis, in order to insert a Shine-Dalgarno sequence (5' AAGGAGATG) upstream of the initiating codon of the INSP035 cDNA. The resultant mutated plasmid was then subjected to a recombination reaction with the E. coli expression vector pDEST14 to create pDEST14-SD-INSP035-6HIS.

3. Insertion of a Shine—Dalgamo Sequence into pENTR-INSP035-6HIS by Site-directed mutagenesis 3.1 Gene Specific Cloning Primers for Site-directed Mutagenesis A pair of PCR primers, INSP035-MF and INSP035-MR (Table 4), were designed such that the primers annealed to opposite strands of the plasmid pENTR-INSP035-6HIS sequence and each primer annealed to 15-25 bases on either side of the region to be inserted. The PCR primers were optimised to have a Tm greater than or equal to 78° C., a minimum GC content of 40%, and either a G or a C as the 3' terminal base. Primers were designed and optimised using Primer Designer Software (Scientific & Educational Software, PO Box 72045, Durham, N.C. 27722-2045, USA). Primers were purified by polyacrylamide gel electrophoresis (PAGE).

3.2 Site-direct Mutagenesis

Site-directed mutagenesis was carried out using the QuikChange® Site-Directed Mutagenesis Kit (Stratagene) according to the manufacturer's Instructions. The mutagenesis reaction was performed using the Quick Change Mutagenesis kit (Stratagene) in a final volume of 50 µl containing:

5 µl of 10X reaction buffer,
100 ng plasmid pENTR-INSP035-6HIS DNA,
125 ng INSP035-MF primer,
125 ng INSP035-MR primer,
1 µl dNTP mix,
3 µl Quick Solution, and
1 µl Pfu Turbo DNA polymerase.

Thermal cycling was performed using a MJ Research DNA Engine, programmed as follows: 95° C., 1 min; 18 cycles of 95° C., 50 sec, 60° C., 50 sec, and 68° C., 3 min; followed by an additional elongation cycle of 68° C. for 7 min and a holding cycle of 4° C.

Dpn I digestion was used to digest the methylated or hemimethylated parental DNA template (plasmid pENTR-INSP035-6HIS in the sample reaction). 1 µl of Dpn I restriction enzyme (10 U/μl, Stratagene) was added to the reaction mixture and incubated at 37° C. for 1 hour. The reaction mixture was then transformed into XL 10-Gold supercompetent cells (Stratagene) as follows. A 50 μl aliquot of XL 10-Gold cells was thawed on ice and 1 μl of Dpn I -treated DNA was added. The mixture was incubated for 30 min on ice and then heat shocked by incubation at 42° C. for exactly 45 s. Samples were returned to ice for 2 min and 250 1 μl of pre-warmed (42° C.) NZY media was added. Samples were incubated with shaking (220 rpm) for 1 h at 37° C. The transformation mixture was plated on L-broth (LB) plates containing kanamycin (40 μg/ml). Plates were incubated overnight at 37° C.

3.3 Plasmid DNA Preparation and Sequencing

Eight colonies from the sample transformation plate were inoculated into 5 ml L-Broth (LB) containing kanamycin (40 μg/ml) and grown up overnight at 37° C. with shaking at 220 rpm. Plasmid mini-prep DNA was prepared using a Qiaprep Turbo 9600 robotic system (Qiagen). Plasmid DNA (150-200 ng) was subjected to DNA sequencing with 21M13 and M13Rev primers using the BigDyeTerminator system (Applied Biosystems cat. no. 4390246) according to the manufacturer's instructions. The primer sequences are shown in Table 4. Sequencing reactions were purified using Dye-Ex columns (Qiagen) or Montage SEQ 96 cleanup plates (Millipore cat. no. LSKS09624) then analyzed on an Applied Biosystems 3700 sequencer.

Sequence analysis identified a clone which contained the sequence of INSP035-6HIS with an upstream Shine Dalgarno sequence.

3.4 Transfer of INSP035-6HIS Coding Sequence from Gateway Donor Mutated Vector (16318) to *E. coli* Expression Vector pDEST14.

Plasmid mini-prep DNA prepared from plasmid containing the sequence of INSP035-6HIS with an upstream Shine Dalgarno sequence (1.5 μl) was then used in a recombination reaction containing 1.5 μl pDEST14 vector (0.1 μg/μl), 2 μl LR buffer and 1.5 μl of LR clonase (Invitrogen) in a final volume of 10 μl. The mixture was incubated at RT for 1 h, stopped by addition of proteinase K (2 μg) and incubated at 37° C. for a further 10 min. An aliquot of this reaction (1 μl) was used to transform *E. coil* DH10B cells by electroporation as follows: a 25 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml) which had been pre-warmed to room temperature was added immediately after electroporation. The mixture was transferred to a 15 ml snap-cap tube and incubated, with shaking (220 rpm) for 1 h at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures from 6 of the resultant colonies using a Qiaprep Turbo 9600 robotic system (Qiagen). Plasmid DNA (200-500 ng) was subjected to DNA sequencing using T7 and pDEST14R primers (Table 4). Mini-prep plasmid DNA from 1 of the resultant clones (pDEST14-SD-INSP035-6HIS) is then used to transform for example *E. coli* BL21 DE3 cells for protein production.

TABLE 4

Sequencing and mutagenesis primers

| Primer | Sequence (5'-3') |
|---|---|
| INSP035-MF | ACA AAA AAG CAG GCT TCG AAG GAG ATG CCA CCA TGT CCC TGG G (SEQ ID NO:13) |
| INSP035-MR | CCC CAG GGA CAT GGT GGC ATC TCC TTC GAA GCC TGC TTT TTT G (SEQ ID NO:14) |
| 21M13 | TGT AAA ACG ACG GCC AGT (SEQ ID NO:15) |
| M13REV | CAG GAA ACA GCT ATG ACC (SEQ ID NO:16) |
| T7 primer | TAA TAC GAC TCA CTA TAG GG (SEQ ID NO:17) |
| pDEST14-R | TGG CAG CAG CCA ACT CAG CTT (SEQ ID NO:18) |

Example 4

Analysis of INSP035 Gene Expression Levels by TaqMan Analysis

Total RNA from each sample was reverse transcribed using the Superscript III First-Strand Synthesis System for RT-PCR (Invitrogen, Cat. No. 18080-051) in a final reaction volume of 20 μl. 2 μg of total RNA was combined with 50 ng random hexamer primers, 10 mM each of dATP, dGTP, dCTP, & dTTP, and DEPC-treated water in a volume of 10 μl. The mixture was incubated at 65° C. for 5 min then chilled on ice for 1 min. The following 10 μl cDNA synthesis mix was prepared in a separate tube: 2 μl 10×RT buffer, 4 μl 25 mM MgCl$_2$, 2 μl 0.1 M DTT, 1 μl RnaseOUT™ (40 units/μl), and 1 μl SuperScript™ III RT enzyme (200 units/μl). The cDNA synthesis mix was added to the RNA/primer mixture, mixed gently and incubated at 25° C. for 10 min then at 50° C. for 50 min. The RT enzyme was then inactivated by incubating at 85° C. for 5 min. The mixture was chilled on ice and then 1 μl of *E. coli* Rnase H (2 units/μl) was added and the mixture incubated at 37° C. for 20 min. The mixture was chilled on ice and then diluted ½50with sterile water. Dilutions of the reverse transcriptase reaction were then subjected to real time PCR analysis on a TaqMan instrument (PE Biosystems 7700).

PCR primers for human INSP035 and the housekeeping control gene glyceraldehyde 3-phosphate dehydrogenase (GAPDH) were designed using the Primer Express software (PE Biosystems). The primers selected were h-INSP035-169F1 (AGGGCCCAAGCCAAACC) (SEQ ID NO:19) and h-INSP035-281R1 (TCCTGCGCCTGCATCTCC) (SEQ ID NO:20). The specificity and the optimal primer concentration to use for the TaqMan analysis were determined by testing the INSP035 gene-specific primers on a series of dilutions of plasmid pCR-XL-TOPO-INSP035. Potential genomic DNA contamination of the cDNA was excluded by performing PCR reactions using primers specific for GAPDH intronic sequence. The absence of non-specific amplification was controlled by analyzing the PCR products on 4% agarose gels to ensure a single band of the expected molecular weight was produced.

SYBR Green Real-Time PCR reactions were carried out in a reaction volume of 50 μl containing 25 μl SYBR Green PCR master mix (PE Biosystems) (to which 0.5 units AmpErase Uracil N-Glycosylase (UNG, PE Biosystems) had previously been added), 300 nM of each amplification primer, and 5 μl of RT-PCR product. Cycling was performed using the ABI PRISM 7700 (TaqMan) Detection System programmed as follows: 1 cycle of 50° C. for 2 min; 1 cycle of 95° C. for 10 min; 40 cycles of 95° C. for 15 sec, 60° C. for 1 min. Each reaction was carried out in duplicate and the results averaged.

The primer-specific regions of the reverse-transcribed cDNA samples were thus amplified and their cycle threshold (Ct) values determined. The Ct value for each cDNA sample was normalized to that of the housekeeping gene GAPDH as follows. The difference in expression level between the GAPDH gene and the INSP035 gene in each cDNA sample was expressed as a difference in Ct value, i.e. Delta (δ) Ct=Ct (GAPDH)−Ct (INSP035). Results for each sample were then expressed as a fold difference in the number of cycles required for detectable INSP035 gene expression relative to that for GAPDH, according to the formula Fold Difference=$2^{(-\delta ct)}$. Finally, the expression level of the INSP035 gene in each cDNA sample was shown relative to the GAPDH gene expression level, where GAPDH expression level=100%, by dividing 100 by the Fold Difference for INSP035. Results are shown in table 5.

TABLE 5

Expression of INSP035 in various human tissues as measured by RT-PCR (TaqMan).

| CDNA | 8A11/8A12 H-GAPDH | 23E5/23E6 H-INSP035 | DELTA CT | FOLD DIFFERENCE | RELATIVE TO GAPDH (=100) |
|---|---|---|---|---|---|
| S76 Brain | 19.58 | 30.94 | −11.36 | 2628.46 | 0.04 |
| S77 Heart | 21.19 | 33.28 | −12.09 | 4359.66 | 0.02 |
| S78 Kidney | 20.93 | 30.84 | −9.91 | 962.07 | 0.10 |
| S79 liver | 21.86 | 28.95 | −7.09 | 136.24 | 0.73 |
| S80 Lung | 22.14 | 30.53 | −8.39 | 335.46 | 0.30 |
| S81 Placenta | 22.36 | 30.94 | −8.58 | 382.68 | 0.26 |
| S82 skeletal Muscle | 17.39 | 31.86 | −14.47 | 22693.63 | 0.00 |
| S83 small intestine | 20.88 | 30.98 | −10.10 | 1097.50 | 0.09 |
| S84 Spleen | 20.40 | 35.31 | −14.91 | 30786.28 | 0.00 |
| S85 Thymus | 20.13 | 31.28 | −11.15 | 2272.40 | 0.04 |
| S86 Uterus | 21.06 | 29.19 | −8.13 | 280.14 | 0.36 |
| S87 Bone Marrow | 22.57 | 33.87 | −11.30 | 2521.38 | 0.04 |
| S88 Thyroid | 20.83 | 30.05 | −9.22 | 596.34 | 0.17 |
| S89 Spinal cord | 20.89 | 32.41 | −11.52 | 2936.74 | 0.03 |
| S90 Cervix | 23.36 | 30.24 | −6.88 | 117.78 | 0.85 |
| S91 colon | 21.61 | 31.14 | −9.53 | 739.29 | 0.14 |
| S92 ovary | 23.21 | 31.49 | −8.28 | 310.83 | 0.32 |
| S93 prostate | 20.56 | 32.73 | −12.17 | 4608.24 | 0.02 |
| S94 testis | 22.21 | 31.11 | −8.90 | 477.71 | 0.21 |
| S95 skin | 23.02 | 31.45 | −8.43 | 344.89 | 0.29 |
| S113 pancreas | 24.15 | 30.87 | −6.72 | 105.42 | 0.95 |
| S115 Salivary gland | 23.21 | 32.84 | −9.63 | 792.35 | 0.13 |
| S116 Adrenal gland | 21.78 | 29.13 | −7.35 | 163.14 | 0.61 |
| S117 Universal h-ref | 16.38 | 30.09 | −13.71 | 13400.51 | 0.01 |
| S119 Breast | 21.50 | 30.94 | −9.44 | 694.58 | 0.14 |
| S120 Stomach | 21.67 | 32.14 | −10.47 | 1418.35 | 0.07 |
| S121 Fetal Kidney | 20.17 | 29.14 | −8.97 | 501.46 | 0.20 |
| S122 Eye | 22.42 | 32.41 | −9.99 | 1016.93 | 0.10 |
| S123 Mammary gland | 21.82 | 32.01 | −10.19 | 1168.14 | 0.09 |
| S124 Ovary | 19.79 | 29.61 | −9.82 | 903.89 | 0.11 |
| S125 Pituitary gland | 22.44 | 31.08 | −8.64 | 398.93 | 0.25 |
| S127 human lupus liver | 23.05 | 33.06 | −10.01 | 1031.12 | 0.10 |
| S128 human lupus Lung | 21.18 | 34.97 | −13.79 | 14164.58 | 0.01 |
| S129 human lupus Spleen | 23.39 | 30.71 | −7.32 | 159.79 | 0.63 |
| S130 human lupus Kidney | 21.76 | 30.69 | −8.93 | 487.75 | 0.21 |
| S131 cirrhosis liver | 20.62 | 32.67 | −12.05 | 4240.45 | 0.02 |
| S132 cirrhosis Lung | 18.22 | 31.42 | −13.20 | 9410.14 | 0.01 |
| S133 cirrhosis Spleen | 22.01 | 32.93 | −10.92 | 1937.53 | 0.05 |
| S134 cirrhosis Small intestine | 19.98 | 31.82 | −11.84 | 3666.02 | 0.03 |
| S135 kidney Tumor | 20.01 | 28.94 | −8.93 | 487.75 | 0.21 |
| S136 Liver Tumor | 19.29 | 31.34 | −12.05 | 4240.45 | 0.02 |
| S137 Lung Tumor | 21.60 | 30.82 | −9.22 | 596.34 | 0.17 |
| S142 Fetal Liver | 20.96 | 29.67 | −8.71 | 418.77 | 0.24 |
| S138 colon Tumor | 19.57 | 30.61 | −11.04 | 2105.58 | 0.05 |
| S140 Fetal brain | 19.89 | 32.10 | −12.21 | 4737.79 | 0.02 |
| S141 Fetal spleen | 21.00 | 32.53 | −11.53 | 2957.17 | 0.03 |
| S139 Breast Tumor | 22.52 | 33.27 | −10.75 | 1722.16 | 0.06 |
| S143 Fetal Heart | 20.29 | 32.94 | −12.65 | 6427.31 | 0.02 |
| S11 mixed RA2 | 21.28 | 30.44 | −9.16 | 572.05 | 0.17 |
| S7 Fibroblast SSCA2 | 19.14 | 31.01 | −11.87 | 3743.05 | 0.03 |
| S6 Fibroblast SSc N2 | 18.20 | 32.22 | −14.02 | 16612.71 | 0.01 |
| S5 Fibroblast NF2 | 21.53 | 30.69 | −9.16 | 572.05 | 0.17 |
| S4 Fibroblast NF1 | 20.13 | 29.35 | −9.22 | 596.34 | 0.17 |
| S3 Fibroblast Clark N | 19.31 | 31.82 | −12.51 | 5832.91 | 0.02 |
| S2 Fibroblast Howard ab | 19.28 | 31.26 | −11.98 | 4039.61 | 0.02 |
| S1 Fibroblast AG1518 | 20.16 | 30.13 | −9.97 | 1002.93 | 0.10 |
| S151 Disease Brain | 21.99 | 31.29 | −9.30 | 630.35 | 0.16 |
| S150 Throat | 20.11 | 33.20 | −13.09 | 8719.32 | 0.01 |

TABLE 5-continued

Expression of INSP035 in various human tissues as measured by RT-PCR (TaqMan).

| CDNA | 8A11/8A12 H-GAPDH | 23E5/23E6 H-INSP035 | DELTA CT | FOLD DIFFERENCE | RELATIVE TO GAPDH (=100) |
|---|---|---|---|---|---|
| S149 Blood vessy Artery | 20.96 | 33.12 | −12.16 | 4576.41 | 0.02 |
| S148 Appendix | 21.65 | 32.42 | −10.77 | 1746.20 | 0.06 |
| S147 Bladder | 21.73 | 30.93 | −9.20 | 588.13 | 0.17 |
| S146 Adipose | 19.47 | 28.95 | −9.48 | 714.11 | 0.14 |
| S145 Lymph Node | 19.88 | 30.06 | −10.18 | 1160.07 | 0.09 |
| S144 Fetal Lung | 16.18 | 28.96 | −12.78 | 7033.37 | 0.01 |
| S67 mixed small intestine UC 18 | 24.38 | 31.87 | −7.49 | 179.77 | 0.56 |
| S65 mixed small intestine Crohn's 7 | 22.18 | 31.52 | −9.34 | 648.07 | 0.15 |
| S64 mixed small intestine Crohn's 8 | 23.42 | 32.94 | −9.52 | 734.19 | 0.14 |
| S63 mixed small intestine normal int 23 | 24.56 | 33.34 | −8.78 | 439.59 | 0.23 |
| S62 mixed small intestine normal int 21 | 21.13 | 33.70 | −12.57 | 6080.61 | 0.02 |
| S52 mixed colon 13073 | 22.34 | 33.72 | −11.38 | 2665.15 | 0.04 |
| S50 mixed colon 13224 | 21.30 | 32.86 | −11.56 | 3019.30 | 0.03 |
| S29 mixed Lung D | 23.05 | 29.41 | −6.36 | 82.14 | 1.22 |
| S28 mixed Lung C | 23.17 | 31.68 | −8.51 | 364.56 | 0.27 |
| S27 mixed Lung A | 25.56 | 32.75 | −7.19 | 146.02 | 0.68 |
| S19 mixed OA4 | 24.05 | 30.80 | −6.75 | 107.63 | 0.93 |
| S18 Fibroblast LA13 | 18.43 | 32.71 | −14.28 | 19893.37 | 0.01 |
| S17 Fibroblast LN14 | 18.55 | 32.40 | −13.85 | 14766.09 | 0.01 |
| S16 Fibroblast LAb1 | 18.01 | 29.59 | −11.58 | 3061.45 | 0.03 |
| S15 Fibroblast LN1 | 20.29 | 31.13 | −10.84 | 1833.01 | 0.05 |
| S12 mixed RA3 | 21.47 | 32.52 | −11.05 | 2120.22 | 0.05 |
| BN5 atherosclerotic plaque Z3 | 25.73 | 34.88 | −9.15 | 568.10 | 0.18 |
| BN3 atherosclerotic plaque Z2 | 24.60 | 32.70 | −8.10 | 274.37 | 0.36 |
| BN1 atherosclerotic plaque Z1 | 22.12 | 30.35 | −8.23 | 300.25 | 0.33 |
| S20 Keratinocytes skin K1 | 20.07 | 32.73 | −12.66 | 6472.02 | 0.02 |
| S21 Keratinocytes skin K2 | 22.53 | 37.78 | −15.25 | 38967.94 | 0.00 |
| S25 LDC lung | 19.09 | 32.57 | −13.48 | 11425.74 | 0.01 |
| S36 THP-1 mono/mac | 19.20 | 33.37 | −14.17 | 18432.96 | 0.01 |
| S13 mixed OA1 | 27.00 | 33.90 | −6.90 | 119.43 | 0.84 |

Defining a threshold of Expression level of INSP035 relative to GAPDH expression of 0.5, TaqMan expression results show that INSP035 is highly expressed in fetal liver, cervix, pancreas, adrenal gland, human lupus spleen, ulcerative colitis mixed small intestine, and particularly in lung. Strong expression in lung and liver supports the involvement of INSP035 in lung and liver fibrosis.

Example 5

INSP035 Administration in vivo Protects Against Bleomycin Induced Lung Fibrosis in Mice Administration of a single intra-tracheal injection bleomycin to C57BL/6 mice results in the rapid induction of pulmonary fibrosis within 14 days, which is characterized by increased collagen deposition within the lung interstitium (Hattori et al., 2000. Zuo et al. 2002. Phillips et al 2004). In order to determine if INSP035 administration could have any protective effect against the development of fibrosis or indeed reduce the severity of the disease, effect of daily injection of INSP035 can be tested in bleomycin treated mice.

In order to complete the experiment, mice are divided into four groups. Bleomycin is administered by a single intra-tracheal instillation to 3 groups of 10 mice. For comparison a 4$^{th}$ group of mice is included in the study which comprises completely untreated, age and sex matched individuals (naïve mice). INSP035 is administered by subcutaneous injection starting the day after bleomycin treatment. One group receives a high bleomycin dose (5 mg/kg), the second group receives a lower bleomycin dose (0.5 mg/kg) and control mice receive saline s.c. daily.

Animals treated with bleomycin should fall sick with rapid loss of body mass leading to death.

All surviving mice are sacrificed 12 days after the bleomycin treatment. Histological analysis of lungs reveals the effect of INSP035 treated animals. Reduced hydroxyproline content should be observed in INSP035 treated mice (hydroxyproline content is a measure of collagen deposition). It can be concluded that INSP035 treatment effectively leads to reduced collagen deposition in the lungs.

REFERENCES

1. Abraham D., Lupoli S., McWhirter A., Plater-Zyberk C., Piela T. H., Korn J. H., Olsen I. and Black C. (1991) Expression and function of surface antigens on scleroderma fibroblasts. Arthritis Rheum. 34, 1164-1172.
2. Abraham D J, Shiwen X, Black C M, Sa S, Xu Y. Leask A. J Biol Chem. 2000 May 19; 275(20):15220-5.
3. Afdhal N H, Nunes D. Am J Gastroenterol. 2004 June; 99(6):1160-74. Review.
4. Altschul S F et al, J Mol Biol, 215, 403-410, 1990
5. Altschul S F et al, Nucleic Acids Res., 25:389-3402, 1997
6. Black C. M and Denton C. P. (1998) Systemic sclerosis and related disorders. In "Oxford textbook of Rheumatology" (P. G. Maddison, D. A. Isenberg, P. Woo and D. N. Glass, Eds.) pp 771-789, Oxford Univ. Press, New York.
7. Clements P. J. and Furst D. E. (1996) "Systemic Sclerosis" Williama and Williams, Baltimore.
8. Chung L, Utz P J. Curr Rheumatol Rep. 2004 April; 6(2):156-63.

9. Devereux J et al, Nucleic Acids Res, 12, 387-395, 1984.
10. Emery J. et al. J. Biol. Chem. 1998. 273:14363-14367.
11. Engelmann, H., Novick, D., and Wallach, D., 1990, J. Biol. Chem. 265, 1531-1536.
12. Granot I, Halevy O, Hurwitz S, Pines M. (1993) Halofuginone: an inhibitor of collagen type I synthesis. Biochim Biophys Acta 1156, 107-112.
13. Grantham (1974), Science, 185.862-864.
14. Hasel C. at al. Lab. Invest. 2003; 83(6):82546.
15. Hattori et al., J. Clin. Invest. 2000.106:1341.
16. Kershenobich Stalnikowitz D, Weissbrod A B. Ann Hepatol. 2003 October-December; 2(4):159-63.
17. Khalil N and O' Connor R. CMAJ 2004.171(2):153-60.
18. Kostenuik P J, Shalhoub V. Curr Pharm Des 2001 May;7(8):61335
19. Krein, P M, Huang Y amd Winston B W (2001). Expert Opin. Ther. Patents 11(7): 1065-1079.
20. Leighton, C. Drugs 2001 61(3), 419427.
21. LeRoy E. C. (1974) Increased collagen synthesis by scleroderma skin fibroblasts in vitro. J. Clin. Invest. 54, 880-889.
22. Martini, Maccario, Ravelli et al., Arthritis Rheum. 1999, 42, 807-811.
23. McGaha T L, Phelps R G, Spiera H, Bona C. (2002) Halofuginone, an Inhibitor of Type-I Collagen Synthesis and Skin Sclerosis, Blocks Transforming-Growth-Factor-beta-Mediated Smad3 Activation in Fibroblasts. J Invest Dermatol. 118,461-70.
24. Min H., Morony S., Sarosi I., Dunstan C. R., Capparelli C. et al (2000) INSP035 reverses osteoporosis by inhibiting endosteal osteodasts and prevents vascular calcification by blocking a process resembling osteoclastogenesis. J. Exp. Med. 192, 463-474.
25. Moringa T., Nagakawa N., Yasuda H., Tsuda E. and Higashi K. (1998) Cloning and characterization of the gene encoding human INSP035/osteoclastogenesis inhibitory factor. Eur. J. Biochem. 254, 685-691.
26. Pearson W R, Methods in Enzymology, 183, 63-99, 1990
27. Pearson W R and Lipman D) J. Proc Nat Acad Sci USA, 85, 2444-2448,1988.
28. Pinzani M, Rombouts K. Dig Liver Dis. 2004 April;36 (4):231-42.
29. Phillips et al. The Journal of Clinical Investigation 2004. 114(3):438-446.
30. Rhew E Y, Barr W G. Curr Rheumatol Rep. 2004 Apr;6(2):129-36.
31. Selman et al Drugs 2004; 64(4):405-30.
32. Shipman C M and Croucher P I. Cancer Res. 2003; 63(5):912-916.
33. Silman A. J. (1991) Moratlity from scleroderma in England and Wales 1968-1975. Ann. Rheu. Dis. 50, 95-96.
34. Simonet W. S., Lacey D.:., Dunstan C. R., Kelley M., et al. (1997) INSP035: a novel secreted protein involved in the regulation of bone densit y. Cell 89, 309-319.
35. Shi-wen X., Denton C. P., McWhirter A., Bou-Gharios G., Abraham D. J., du Bois R. M. and Black C. M. (1997) Scleroderma lung fibroblasts exhibit elevated and dysregulated collagen type I biosynthesis. Arthritis Rheum. 40, 1237-1244.
36. Smith and Waterman J Mol Biol, 147,195-197, 1981, Advances in Applied Mathematics, 2, 482-489, 1981.
37. Smith R. E., Strieter R. M., Phan S. H., Lukacs N. W., Huffnagle G. B., Wilke C. A., Burdick M. D., Lincoln P., Evanoff H. and Kunkel S. L. (1994) Production and function of murine macrophage inflammatory protein-1α in bleomycin induced lung injury. J. Immunol. 1.53, 4704.
38. Smith, Textbook of the Autoimmune Diseases, Edited by Lahita, Chiorazzi and Reeves, Lippincott Williams & Wilkins, Philadelphia 2000.
39. Strehlow D. and Kom J (1998) Biology of the scleroderma fibroblast. Curr. Opin. Rheumatol. 10, 572-578.
40. Taimr P. et al. Hepatology 2003. 37(1):87-95.
41. Tucci, A., James, H., Chicheportiche, R., Bonnefoy, J. Y., Dayer, J. M., and Zubler, R. H., 1992, J. Immunol. 148, 2778-2784.
42. Varga J. Curr Rheumatol Rep. 2004 April; 6(2):164-70.
43. Walczak H. et al. EMBO J. 1997.16:5386-5397.
44. Wigley F. M. and Sule S. D. (2001) Expert Opinions on Investigational Drugs 10(1) 31-48.
45. Wigley F. M. and Boling C. L. (2000) The treatment of sleroderma. 2, 276-292.
46. Yasuda H., Shima N., Nagakawa N., Mochizuki S., Yano K. et al (1998) Identity of osteoclastogenesisis inhibitory factor (OCIF) and osteoprotegerin (OPG): a mechanism by which OPG/OCIF inhibits osteoclastogenesis in vitro. Endocrinology 139, 1329-1337.
47. Yurovsky V V. Am. J. Respir. Cell. Mol. Biol. 2003. 28(2):225-31.
48. Zuo et al. PNAS 2002.99 :6292-6297.

The invention claimed is:

1. A method for treating a fibrotic disease comprising administering to a patient having a fibrotic disease a therapeutically effective amount of a composition comprising a pharmaceutically acceptable carrier and a polypeptide comprising SEQ ID NO: 2, SEQ ID NO: 5 or SEQ ID NO: 7, wherein said fibrotic disease is lung fibrosis or liver fibrosis.

2. The method according to claim 1, wherein the fibrotic disease is lung fibrosis.

3. The method according to claim 1, wherein the polypeptide is glycosylated at one or more sites.

4. The method according to claim 1, wherein the polypeptide comprising SEQ ID NO: 2 is a fusion protein.

5. The method according to claim 4, wherein the fusion protein comprises an immunoglobulin Fc region fused to SEQ ID NO: 2.

6. The method according to claim 1, wherein the polypeptide consists of SEQ ID NO: 2.

7. The method according to claim 1, wherein the composition further comprises an interferon.

8. The method according to claim 7, wherein the interferon is interferon-β.

9. The method according to claim 1, wherein a composition comprising an interferon is administered to said patient simultaneously, sequentially, or separately with a composition comprising a pharmaceutically acceptable carrier and SEQ ID NO: 2.

10. The method according to claim 1, wherein said fibrotic disease is liver fibrosis.

11. The method according to claim 1, wherein said composition comprises a pharmaceutically acceptable carrier and a polypeptide comprising SEQ ID NO: 2.

12. The method according to claim 1, wherein said composition comprises a pharmaceutically acceptable carrier and a salt of a polypeptide comprising SEQ ID NO: 2.

13. The method according to claim 12, wherein said salt is a sodium, calcium, ammonium, ferric or zinc salt.

14. The method according to claim 12, wherein said salt is a triethanolamine, arginine, lysine, piperidine or procaine salt.

15. The method according to claim 12, wherein said salt is an acid addition salt.

16. The method according to claim 15, wherein said acid addition salt is formed by the addition of hydrochloric, sulfuric, acetic or oxalic acid.

17. The method according to claim 1, wherein said polypeptide comprising SEQ ID NO: 5 is a fusion protein.

18. The method according to claim 17, wherein the fusion protein comprises an immunoglobulin Fc region fused to SEQ ID NO: 5.

19. The method according to claim 1, wherein the polypeptide consists of SEQ ID NO: 5.

20. The method according to claim 1, wherein said polypeptide comprising SEQ ID NO: 7 is a fusion protein.

21. The method according to claim 17, wherein the fusion protein comprises an immunoglobulin Fc region fused to SEQ ID NO: 7.

22. The method according to claim 1, wherein the polypeptide consists of SEQ ID NO: 7.

23. The method according to claim 1, wherein a composition comprising an interferon is administered to said patient simultaneously, sequentially, or separately with a composition comprising a pharmaceutically acceptable carrier and SEQ ID NO: 5.

24. The method according to claim 1, wherein a composition comprising an interferon is administered to said patient simultaneously, sequentially, or separately with a composition comprising a pharmaceutically acceptable carrier and SEQ ID NO: 7.

25. The method according to claim 1, wherein said composition comprises a pharmaceutically acceptable carrier and a polypeptide comprising SEQ ID NO: 5.

26. The method according to claim 1, wherein said composition comprises a pharmaceutically acceptable carrier and a polypeptide comprising SEQ ID NO: 7.

27. The method according to claim 1, wherein said composition comprises a pharmaceutically acceptable carrier and a salt of a polypeptide comprising SEQ ID NO: 5.

28. The method according to claim 27, wherein said salt is a sodium, calcium, ammonium, ferric or zinc salt.

29. The method according to claim 27, wherein said salt is a triethanolamine, arginine, lysine, piperidine or procaine salt.

30. The method according to claim 27, wherein said salt is an acid addition salt.

31. The method according to claim 30, wherein said acid addition salt is formed by the addition of hydrochloric, sulfuric, acetic or oxalic acid.

32. The method according to claim 1, wherein said composition comprises a pharmaceutically acceptable carrier and a salt of a polypeptide comprising SEQ ID NO: 7.

33. The method according to claim 32, wherein said salt is a sodium, calcium, ammonium, ferric or zinc salt.

34. The method according to claim 32, wherein said salt is a triethanolamine, arginine, lysine, piperidine or procaine salt.

35. The method according to claim 32, wherein said salt is an acid addition salt.

36. The method according to claim 35, wherein said acid addition salt is formed by the addition of hydrochloric, sulfuric, acetic or oxalic acid.

* * * * *